US011426592B2

(12) United States Patent
Xiao et al.

(10) Patent No.: US 11,426,592 B2
(45) Date of Patent: Aug. 30, 2022

(54) FUNCTIONALITY MIGRATION

(71) Applicant: Cochlear Limited, Macquarie University (AU)

(72) Inventors: Harry Xiao, Macquarie University (AU); Jan Patrick Frieding, Macquarie University (AU); Kenneth Oplinger, Macquarie University (AU); Rishubh Verma, Macquarie University (AU); Martin Evert Gustaf Hillbratt, Mölnlycke (SE); Michael Trieu, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1066 days.

(21) Appl. No.: 15/010,207

(22) Filed: Jan. 29, 2016

(65) Prior Publication Data
US 2016/0331964 A1 Nov. 17, 2016

Related U.S. Application Data

(60) Provisional application No. 62/161,559, filed on May 14, 2015.

(51) Int. Cl.
*A61N 1/36* (2006.01)
*A61N 1/372* (2006.01)

(52) U.S. Cl.
CPC ..... *A61N 1/37247* (2013.01); *A61N 1/36038* (2017.08); *A61N 1/37252* (2013.01); *A61N 1/37258* (2013.01)

(58) Field of Classification Search
CPC ....... A61N 1/05; A61N 1/36032; A61B 5/073
See application file for complete search history.

(56) References Cited

U.S. PATENT DOCUMENTS

| 5,721,783 A | 2/1998 | Anderson |
| 6,308,101 B1 | 10/2001 | Faltys |
| 7,412,288 B2 | 8/2008 | Berg |
| 7,630,772 B1 | 12/2009 | Walsh |

(Continued)

FOREIGN PATENT DOCUMENTS

| CN | 2471043 Y | 1/2002 |
| CN | 201893928 U | 7/2011 |

(Continued)

OTHER PUBLICATIONS

International Search Report and Written Opinion for PCT/IB2016/052791, dated Sep. 12, 2016.

(Continued)

*Primary Examiner* — Michael J D'Abreu
(74) *Attorney, Agent, or Firm* — Pilloff Passino & Cosenza LLP; Martin J. Cosenza

(57) ABSTRACT

A sensory supplement medical device, including a stimulation device configured to implement a first functionality of the sensory supplement medical device corresponding to the providing of sensory supplement to a recipient to evoke a sensory percept, wherein the sensory supplement medical device is configured to implement a secondary functionality different from the first functionality, and the sensory supplement medical device is configured to migrate the second functionality to a device remote from the sensory supplement medical device.

24 Claims, 13 Drawing Sheets

(56) References Cited

U.S. PATENT DOCUMENTS

| | | |
|---|---|---|
| 7,929,722 B2 | 4/2011 | Shridhar |
| 2007/0055321 A1 | 3/2007 | Gordon et al. |
| 2010/0172524 A1 | 7/2010 | Durant |
| 2010/0208631 A1* | 8/2010 | Zhang ............... H04L 5/14 370/297 |
| 2012/0095528 A1 | 4/2012 | Miller |
| 2012/0275629 A1 | 11/2012 | Meskens et al. |
| 2013/0315428 A1 | 11/2013 | Perkins et al. |
| 2013/0343585 A1* | 12/2013 | Bennett ............ H04R 25/554 381/315 |
| 2014/0203950 A1* | 7/2014 | Zdeblick ......... G06F 19/3418 340/870.07 |
| 2015/0036853 A1* | 2/2015 | Solum ............. H04R 25/558 381/315 |
| 2015/0119635 A1* | 4/2015 | Gustafsson ........ A61F 11/045 600/25 |
| 2015/0230032 A1* | 8/2015 | Petersen ............ H04R 25/30 381/60 |
| 2015/0230036 A1* | 8/2015 | Pedersen ........... H04R 1/1041 381/330 |
| 2016/0112811 A1* | 4/2016 | Jensen ............ G10L 21/0232 381/17 |

FOREIGN PATENT DOCUMENTS

| | | |
|---|---|---|
| CN | 103328041 A | 9/2013 |
| KR | 20090065718 A | 6/2009 |
| WO | 97/01314 A1 | 1/1997 |

OTHER PUBLICATIONS

Office Action in Chinese Application No. 201680041705.5, dated Sep. 23, 2019.
Extended European Search Report for EP Application No. 16792288.9, dated Jan. 8, 2019.
Office Action in Chinese Application No. 201680041705.5, dated May 8, 2020.

* cited by examiner

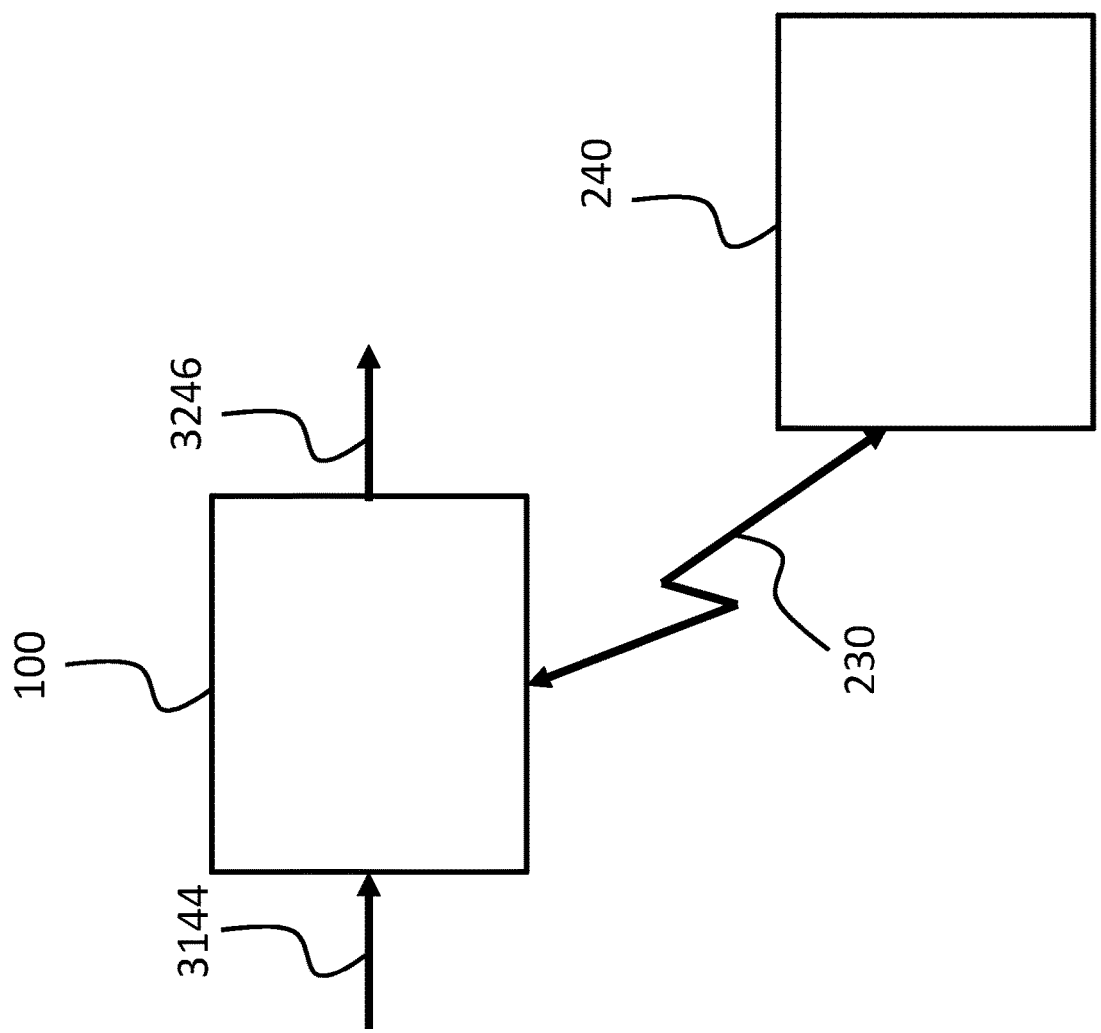

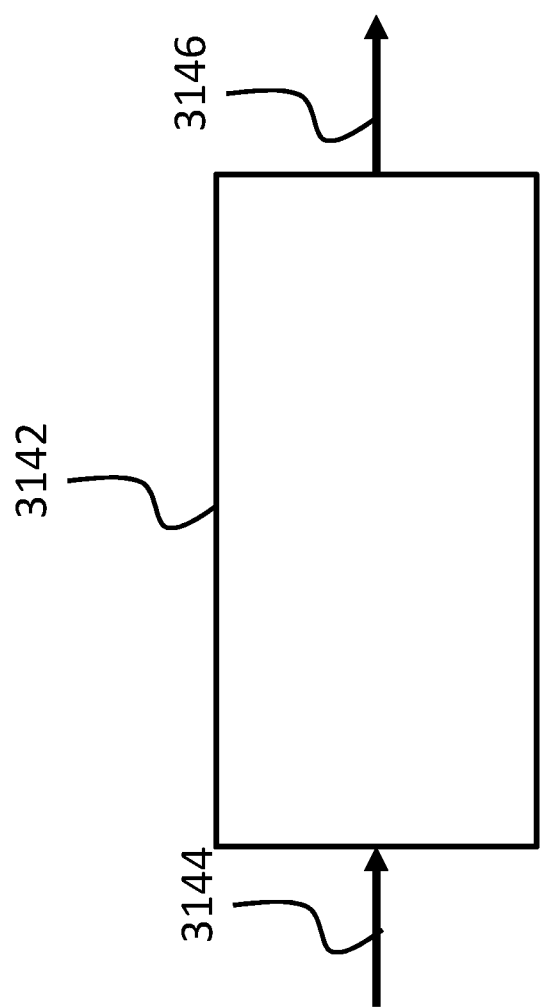

FUNCTIONALITY MIGRATION

CROSS-REFERENCE TO RELATED APPLICATIONS

This application claims priority to Provisional U.S. Patent Application No. 62/161,559, entitled FUNCTIONALITY MIGRATION, filed on May 14, 2015, naming Kenneth OPLINGER of Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is a sensory supplement medical device, comprising a stimulation device configured to implement a first functionality of the sensory supplement medical device corresponding to the providing of sensory supplement to a recipient to evoke a sensory percept, wherein the sensory supplement medical device is configured to implement a secondary functionality different from the first functionality, and the sensory supplement medical device is configured to migrate the second functionality to a device remote from the sensory supplement medical device.

In accordance with another exemplary embodiment, there is a system, comprising a hearing prosthesis including a stimulation device configured to be attached to a recipient and configured to execute one or more functions to evoke a hearing percept and a remote device configured to be portable and configured to wirelessly communicate with the hearing prosthesis, wherein the remote device is configured to perform at least one function of the one or more functions of the hearing prosthesis in lieu of the hearing prosthesis performing that function and communicate the results of that one or more function to the hearing prosthesis via the wireless communication to enable the hearing prosthesis to evoke the hearing percept.

In accordance with another exemplary embodiment, there is a method, comprising at least one of transferring to or simulating by a hearing prosthesis a first functionality of a portable hand-held device having a cellular telephone communication suite and at least one of respectively executing or simulating the first functionality by the hearing prosthesis.

In accordance with another exemplary embodiment, there is a portable hand-held device, comprising a cellular telephone communication suite a hearing prosthesis functionality suite, wherein the hearing prosthesis functionality suite is configured to at least one of perform or simulate a functionality of a hearing prosthesis, the portable hand-held device is configured to wirelessly communicate with the hearing prosthesis.

BRIEF DESCRIPTION OF THE DRAWINGS

Embodiments are described below with reference to the attached drawings, in which:

FIG. 3A presents an exemplary functional arrangement detailing communication between a hearing prosthesis and a remote device;

FIG. 3C presents an exemplary functionality of a black box of the hearing prosthesis according to an exemplary embodiment;

DETAILED DESCRIPTION

Figure 1:
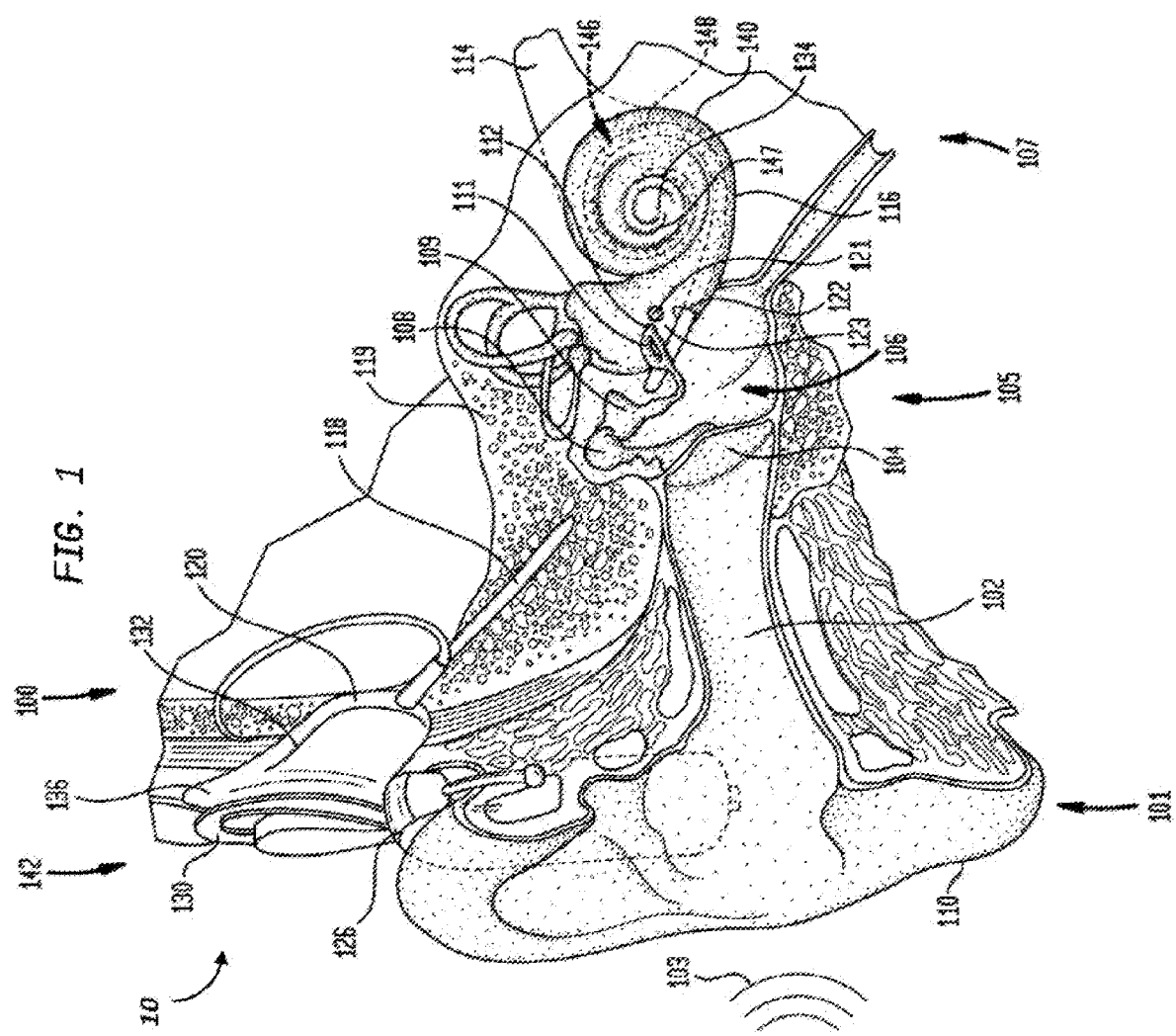
FIG. 1 is a perspective view of an exemplary hearing prosthesis in which at least some of the teachings detailed herein are applicable.

FIG. 1 is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to other types of hearing prosthesis, such as by way of example only and not by way of limitation, bone conduction devices, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof that can have utility can be used in some embodiments of the teachings detailed herein.

In view of the above, it is to be understood that at least some embodiments detailed herein and are variations thereof are directed towards a body-worn sensory supplement medical device (e.g., the hearing prosthesis of FIG. 1, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 2:
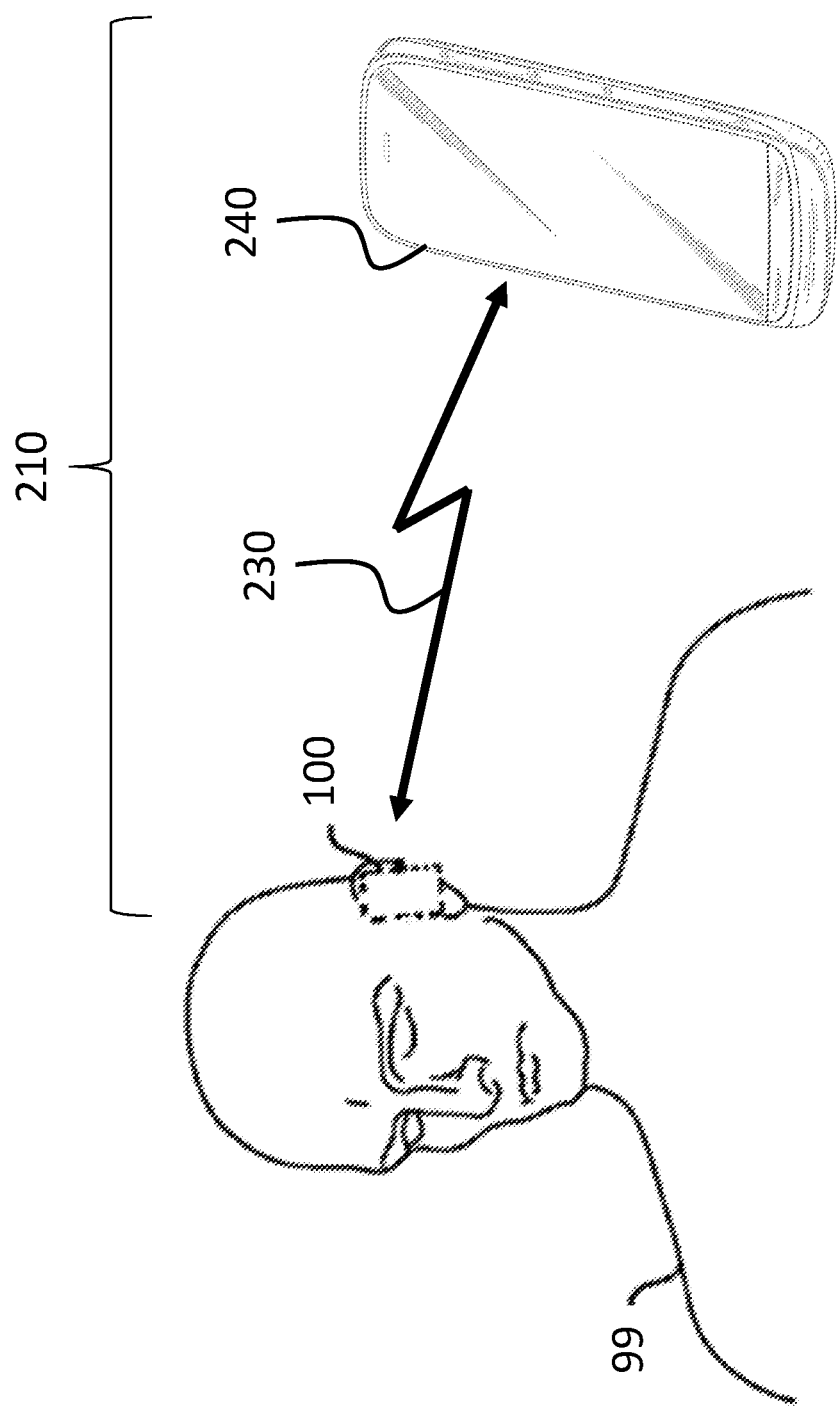
FIG. 2 presents an exemplary system including a hearing prosthesis and a remote device in the form of a portable hand-held device.

FIG. 2 depicts an exemplary system 210 according to an exemplary embodiment, including hearing prosthesis 100, which, in an exemplary embodiment, corresponds to cochlear implant 100 detailed above, and a portable handheld device 240 having a wireless link 230 with the hearing prosthesis 100. In an exemplary embodiment, the hearing prosthesis 100 is an implant implanted in recipient 99 (as represented functionally by the dashed lines of box 100 in FIG. 2). In an exemplary embodiment, the system 210 is configured such that cochlear implant 100 and the portable handheld device 240 (e.g., a portable cellular telephone, such as by way of example only and not by way of limitation, a smart phone as that phrase is utilized generically) have a symbiotic relationship. By way of example only and not by way of limitation, in an exemplary embodiment, the symbiotic relationship is the ability to transfer/a component functionality (e.g., a functionality of the hearing prosthesis 100, a functionality of the portable handheld device 240) between the hearing prosthesis 100 and the portable handheld device 240 via the wireless link 230.

It is noted that while the embodiments detailed herein will be described in terms of utilization of a cochlear implant, alternative embodiments can be utilized other types of hearing prostheses, such as by way of example only and not by way of limitation, bone conduction devices (percutaneous, active transcutaneous and/or passive transcutaneous), Direct Acoustic Cochlear Implants (DACI), and conventional hearing aids. Accordingly, any disclosure herein with regard to one of these types of hearing prostheses corresponds to a disclosure of another of these types of hearing prostheses or any other prosthetic medical device for that matter, unless otherwise specified, or unless the disclosure thereof is incompatible with a given hearing prosthesis based on the current state of technology.

Some exemplary functionalities of the hearing prosthesis 100 that can be transferred/migrated will now be described. That is, some functionalities of the hearing prosthesis 100 will be described, and, in at least some embodiments, the system 210 is configured such that one or more or all of these functionalities can be transferred from the hearing prosthesis to the portable handheld device 240.

By way of example only and not by way of limitation, in an exemplary embodiment, the functionality of data indication (e.g., system status, warnings, alarms, etc.) of the hearing prosthesis 100 can be transferred to the portable handheld device 240. For example, in at least some embodiments, the external component of the hearing prosthesis 100 (e.g., the BTE 126 with reference to the cochlear implant 100 detailed above) is configured with displays, such as by way of example only and not by way of limitation, LEDs, that provide an indicator of a given scenario in which the hearing prosthesis 100 identifies itself. For example, the hearing prosthesis 100 can be configured to provide an LED indication that the RF coil and/or telecoil of the hearing prosthesis that enables the transcutaneous transmission of data from the external component of the hearing prosthesis to the implantable component of the hearing prosthesis, is not aligned or otherwise not in utilitarian proximity to the implantable telecoil and/or that the telecoil cable has been disconnected or that there otherwise is a break in the communication circuit between the output of the processors of the external component of the hearing prosthesis, and the stimulation device of the implantable component of the hearing prosthesis. Still further, the hearing prosthesis 100 can be configured to provide an LED indication that the wrong acoustic component is being used with the hearing prosthesis 100 and/or that the acoustic component has become disconnected or otherwise is no longer in utilitarian communication with other pertinent components of the hearing prosthesis, thus frustrating the ability the hearing prosthesis to evoke a hearing percept in a utilitarian manner.

It is noted that in alternative embodiments, LCD data display can be utilized by the hearing prosthesis 100 instead of, or in addition to, the LEDs. Still further, it is noted that in an alternative embodiment, tones or the like can be utilized by the hearing prosthesis. Still further, in an alternate embodiment, the hearing prosthesis has the functionality of displaying or otherwise providing an indication to the recipient (visually, audibly, etc.) which features of the hearing prosthesis are active. For example, in an exemplary embodiment, hearing prosthesis 100 has the functionality of providing indication(s) the recipient that the hearing prosthesis is evoking a hearing percept based on audio streaming. In an exemplary embodiment, some and/or all of these functionalities (albeit potentially in a different medium, as will be detailed below) can be migrated to the portable handheld device 240 (sometimes referred to as remote device herein).

Still further by example, in an exemplary embodiment, the hearing prosthesis 100 has the functionality of providing an indication of the recipient of which mode in which the prosthesis is operating. By way of example, the hearing prosthesis can provide an indication to the recipient that the hearing prosthesis is operating in a scene classifying mode/ sound classifying mode and/or can provide an indication to the recipient of the classification of the scene classified by the hearing prosthesis. Still further by way of example, in an exemplary embodiment, the hearing prosthesis 100 has the functionality of being able to provide an indication to the recipients of whether or not noise reduction features have been enabled and/or whether or not noise cancellation features have been enabled. Corollary to this is that in at least some embodiments, the hearing prosthesis has the functionality of providing an indication of the recipient of how "hard" the noise reduction system and/or sound cancellation system is operating (e.g., the power consumption resulting from the application of the sound cancellation system, an indication that the sound cancellation system is consuming an inordinate amount of power based on circumstances, etc.). In at least some embodiments, a functionality of the hearing prosthesis is the ability to convey data to a recipient utilizing any technology currently enabled by the art to do so.

In some embodiments, any display functionality and/or any status communication functionality of the hearing prosthesis can be migrated to the portable handheld device 240. Thus, in at least some embodiments, the hearing prosthesis is configured to migrate one or more of these aforementioned functionalities to the portable handheld device 240.

As mentioned above, in at least some exemplary embodiments, the hearing prosthesis includes the functionality of providing an alert to the recipient. Such alerts can include, by way of example only and not by way of limitation, an indication to the recipient that the external component hearing prosthesis has been dropped or otherwise subjected to a shock that may have or indeed did damaged the components thereof. (In an exemplary embodiment, such alerts can include an indication of the recipient that the internal component of the hearing prosthesis may have been damaged and/or has been damaged as a result of the shock or the like.) Still further by way of example, in an exemplary embodiment, the prosthesis has the functionality of providing an indication pertaining to input levels associated with the hearing prosthesis, such as those related to amplitude (the prosthesis determines that an input is too loud or too soft, etc.) and/or quality of noise (e.g., the prosthesis determines that it is not receiving enough speech content) and/or can provide an alert to the recipient regarding input levels into the hearing prosthesis.

Additionally, some exemplary alerts provided by the hearing prosthesis to the recipient include an indication that the prosthesis has gotten wet or otherwise has been subject to a moisture level that may have and/or did imparted damage to one or more components thereof. Alternatively and/or in addition to this, in an exemplary embodiment, the hearing prosthesis is configured to provide an alarm to the recipient that includes an indication that the prosthesis is becoming too hot (overheating) or otherwise reaching a temperature that may damage components thereof. Alternatively and/or in addition to these features, in an exemplary embodiment, an exemplary alert provided to the recipient by the hearing prosthesis entails an alert indicating that the prosthesis has gone out of range of another component associated with the system 210 (e.g., the portable handheld device 240).

Still further, in an exemplary embodiment, the system 210 is configured to migrate the functionality of a given input device of the hearing prosthesis 100 (e.g., the input device is a button, a heat sensitive pad, etc., alone or in combination with another output device, such as an LED) to the portable handheld device 240. By way of example only and not by way of limitation, the input device could be a knob on the BTE device 246 that is adjusted by the recipient to increase or decrease the perceived volume of the resulting hearing percept evoked by the hearing prosthesis 100. The functionality of this knob thus being the control, or at least adjustment, of the perceived volume. In an exemplary embodiment, the hearing prosthesis is configured such that this functionality can be migrated to the portable handheld device 240. Thus, in an exemplary embodiment, the hearing prosthesis is configured to migrate one or more or all of the functionalities of one or more or all of the hearing prosthesis interface components to the portable handheld device upon user selection and/or automatically. Still further, in an exemplary embodiment, functions such as those that result in turning the processor of the hearing prosthesis on and off, changing maps of the hearing prosthesis and/or the initiation and/or halting of streaming data can be migrated to the portal handheld device 240.

It is noted that the migrated functions detailed in the preceding paragraph are not processing functions. That is, no processing is required to execute these functions. Instead, these functions control or otherwise adjust the processing functionality hearing prosthesis. In at least some exemplary embodiments, system 210 is configured to transfer or otherwise migrate processor-based functionalities, and in some instances, to only transfer or otherwise migrate processor-based functionalities.

It is noted that migration of functionality can entail achieving the functionality through the use of technology on the portable handheld device 240 different from that utilized on/by the hearing prosthesis 100. By way of example only and not by way of limitation, in an exemplary embodiment, a warning regarding low battery status may be provided via an LED on an external component of the hearing prosthesis. Conversely, the migration of this functionality to the portable handheld device 240 can result instead in a text message provided on an LCD screen of the portable handheld device 240 stating that the battery charge level is low. Some exemplary technologies of implementing such functionality on the portable handheld device 240 are described below. Briefly however, it is noted that any technology that will enable the functionality of the hearing prosthesis to be at least simulated by the portable handheld device 240 can be practiced to implement the migration of functionality, at least in some embodiments.

Thus, in an exemplary embodiment, there is a hearing prosthesis such as by way of example only and not by way of limitation, cochlear implant 100, comprising a stimulation device (e.g., receiver-stimulator) configured to implement a first functionality of the hearing prosthesis corresponding to the providing of stimulation to tissue of a recipient to evoke a hearing percept. (It is noted that in alternative embodiment, such as by way of example only and not by way of limitation, where the hearing prosthesis is a bone conduction device, the stimulation device can be an actuator, such as by way of example only and not by way of limitation, an electromagnetic actuator.) Still with regard to this exemplary embodiment, the hearing prosthesis is configured to implement a second functionality different from the first functionality. By way of example only and not by way of limitation, with reference to the above, this second functionality can be any functionalities of a hearing prosthesis detailed herein, other than the stimulation functionality, such as the functionality of providing data to the recipient indicative of a status of one or more components of the hearing prosthesis (e.g., battery level, power consumption by a sound classification system, etc.). Still with regard to this exemplary embodiment, the hearing prosthesis is configured to migrate the second functionality to a device remote from the hearing prosthesis (e.g., migrate the functionality to the portable handheld device 240).

In at least some exemplary embodiments of this exemplary embodiment, the device remote from the hearing prosthesis (the portable handheld device 240) is a non-hearing prosthesis device. That is, in an exemplary embodiment, the device remote from the hearing prosthesis is a device that is not required for the hearing prosthesis to operate, even on an extended basis (e.g., for weeks), and is not part of a diagnostic and/or a telemetry device and/or service device that is utilized with the hearing prosthesis. As detailed above, in an exemplary embodiment, the device remote from the hearing prosthesis is a portable handheld device 240 in the form of the smart phone, as that term is generically utilized.

Also as noted above, in an exemplary embodiment, the migrated functionality can be the functionality of alerting the recipient that a given scenario has occurred with respect to the hearing prosthesis. By way of example only and not by way of limitation, the alert can be an alert indicating that the transcutaneous communication link of the hearing prosthesis between the implantable component thereof and an external component thereof is at least partially disrupted (e.g., because the telecoil is not in the proper location/the telecoil and/or RF coil has fallen off the head of the recipient, etc.). Alternatively and/or in addition to this, by way of example only and not by way of limitation, the alert can be an alert indicating that a signal from an acoustical component of the hearing prosthesis has not been and/or is not being received in a sufficient manner such that the functionality of the hearing prosthesis to evoke a hearing percept or the like cannot be enabled, at least not in a utilitarian manner. Still further by way of example, the alert can be an alert indicating that the hearing prosthesis has experienced some type of fault. For example, the fault can be a software fault, or the like. Any functionality that provides an alert to the recipient can be migrated to the portable handheld device 240 in at least some embodiments.

As noted above, in an exemplary embodiment, the hearing prosthesis can be configured in some embodiments to migrate a functionality to the portable handheld device 240 upon a trigger event. In an exemplary embodiment, the trigger event could be recipient selection of the migration. In some alternate embodiments, the migration of the functionality can be automatic. In this regard, a user can provide input into the system 210 (via the hearing prosthesis 100 and/or the portable handheld device 240) to instruct the system 210 to migrate the functionality upon the occurrence of a given scenario. By way of example only and not by way of limitation, such a trigger can be the occurrence of a low battery level of the external component of the hearing prosthesis. Still further, in an exemplary embodiment, the system 210 can be configured to provide an intelligent determination of the utility of migrating the functionality. By way of example only and not by way of limitation, the hearing prosthesis 100 can be configured to make a determination that the power storage device of the hearing prosthesis 100 has achieved a predetermined status (e.g., 90% of the total power storage has been exhausted, continued use of the prosthesis at the current rate will result in the prosthesis being able to evoke a hearing percept for no more than 15 additional minutes, etc.) and also configured to determine that the migration of the functionality will prolong another functionality of the hearing prosthesis (e.g., prolong the ability of the hearing prosthesis to evoke a hearing percept), at least relative to that which would be the case in the absence of the migration of the functionality. Corollary to this is that in at least some embodiments, the system is configured to prevent the automatic migration of the functionality if such will not prolong the other functionality of the hearing prosthesis, at least relative to that which would be the case with the migration of the functionality. By way of example only and not by way of limitation, in at least some embodiments, as will be detailed below, the functionality of sound processing can be migrated from the hearing prosthesis 100 to the portable handheld device 240. The system 210 can be configured such that the system 210 can determine that the migration will result in the temporal prolonging of the ability of the hearing prosthesis to evoke a hearing percept vis-à-vis power consumption, and thus determine to proceed with the migration. The system can also be configured such that the system can determine that the migration will not result in the temporal prolonging of the ability of the hearing prosthesis to evoke a hearing percept vis-à-vis power consumption (which includes a determination that the migration will result in a temporal reduction in the ability of the hearing prosthesis to evoke a hearing percept), and thus determine to not proceed with the migration. That is, in an exemplary embodiment, the hearing prosthesis 100 can be configured to perform an assessment of whether the migration will be less power intensive relative to that which would be the case in the absence of migration, and proceed accordingly.

In at least some embodiments, the system 210 is configured so as to automatically migrate a functionality from the remote device 240 back to the hearing prosthesis 100 upon the occurrence of another triggering event, such as, by way of example only and not by way of limitation, a determination that the scenario that existed that resulted in the original triggering of the migration is no longer present (e.g., the battery of the hearing prosthesis 100 has been recharged or is no longer at a given charge level, or that the hearing prosthesis 100 no longer relies solely on that battery to power the hearing prosthesis (e.g., another power source has been provided, such as a power source that both charges the battery and supplies power to the hearing prosthesis), etc.). Still further, in an exemplary embodiment, the system 210 can be configured to automatically migrate a functionality back after a migration has occurred upon a determination at a later point after the initial migration that the utilitarian value associated with the initial migration is no longer present and/or upon a determination that superseding events have changed the initial conditions upon which it was determined that the migration would be utilitarian.

Any triggering event that can have utilitarian value with respect to automatically triggering an automatic migration of the functionality from the hearing prosthesis 100 to the remote device 240 can be utilized in at least some embodiments. (Some additional exemplary triggering events are described later in this disclosure.)

Still further, it is noted that in at least some embodiments, the hearing prosthesis 100 (and thus the system 210) is configured to automatically select between various functional migration modes. That is, the hearing prosthesis 100 can be configured to select one functional migration over another functional migration, depending on which functional migration will yield increased utilitarian value (e.g., depending on a given set of circumstances, which functional migration will be less power intensive relative to other functional migrations). Still further, in an exemplary embodiment, it is noted that the hearing prosthesis 100 can be configured to automatically select more than one functional migration mode. That is, the hearing prosthesis 100 can be configured to select two or more functional migrations and functionally migrate those functions to the portable handheld device 240 upon an automatic determination that the migration of two or more functions will be more utilitarian than the migration of only one function or fewer functions than the functions ultimately determined to migrate. Still further, in an exemplary embodiment, the hearing prosthesis is configured to automatically perform an assessment of a status of at least one of the hearing prosthesis (e.g., battery level, signal quality from sound capture device, etc.) or the device remote from the hearing prosthesis (battery level, signal quality from the remote device via the wireless link 230, etc.) and prevent the automatic migration of a functionality based on the assessment.

Moreover, in an exemplary embodiment, the hearing prosthesis 100 is configured to automatically suspend further execution of one or more functions upon a determination that a power level of a power storage device thereof meets a given criteria, and the remote device is configured to automatically initiate execution of the one or more functions and communicate the results of that one or more function to the hearing prosthesis, via the wireless communication, to enable the hearing prosthesis to evoke the hearing percept upon the determination that the power level of the power storage device thereof meets the given criteria. Accordingly, in an exemplary embodiment, the system 210 is configured to avoid further taxing a depleted power source of the remote device, at least automatically. In an exemplary embodiment, the system 210 can be configured such that the recipient can override these features and transfer the functionality if such is deemed by the recipient to be utilitarian.

In view of the above, it can be seen that an exemplary embodiment of system 210 includes a hearing prosthesis, such as hearing prosthesis 100, including a stimulation device configured to be attached to a recipient and configured to execute one or more functions to evoke a hearing percept. The system 210 further includes a remote device 240 configured to be portable and configured to wirelessly communicate with the hearing prosthesis, such as, by way of example and not by way of limitation, a smart phone as that term is utilized generically. In an exemplary embodiment, the remote device 240 is configured to perform at least one function of the one or more functions of the hearing prosthesis 100 in lieu of the hearing prosthesis performing that function (although in other embodiments, the migrated/transferred function can still be performed by the transferor) and communicate the results of that one or more function to the hearing prosthesis via the wireless communication to enable the hearing prosthesis 100 to evoke the hearing percept.

Figure 3B:
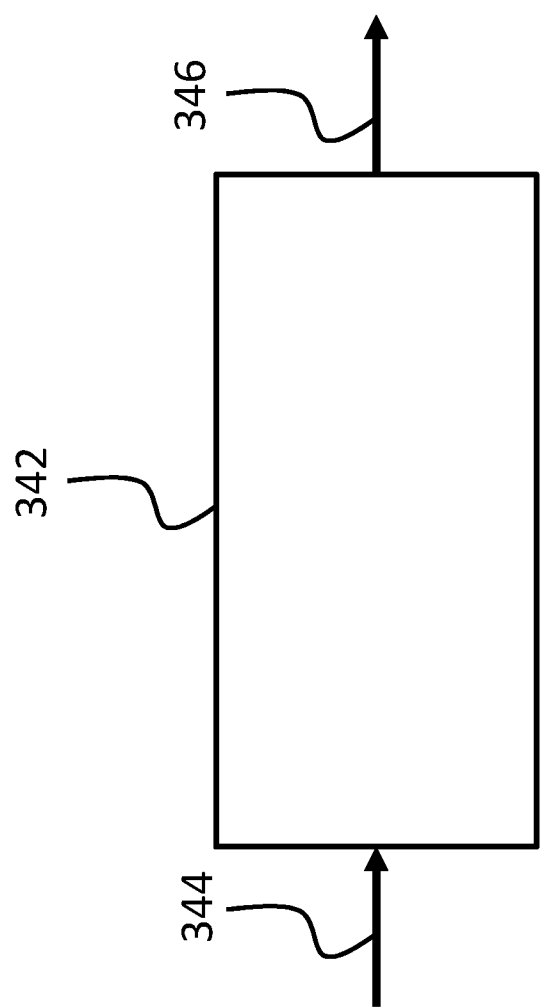
FIG. 3B presents an exemplary functionality of a black box of the remote device according to an exemplary embodiment.

In an exemplary embodiment, the function of the hearing prosthesis that is performed by the remote device as a result of migration thereto from the hearing prosthesis is sound processing of the captured sound. In an exemplary embodiment, the hearing prosthesis 100 captures sound via the microphone on, for example, the BTE 126, and transmits data to the remote device 240 corresponding to a raw output signal of the microphone via link 230. This is functionally represented by FIG. 3A, which depicts the hearing prosthesis 100 and remote device 240 in black box format, where input 3144 corresponds to input into the microphone of the prosthesis 100. (An exemplary algorithm utilizing the functionality of FIG. 3A is detailed below in view of FIG. 5.)

The remote device 240 receives the raw signal via link 230, and processes the data in a manner in the same way as the sound processor of the hearing prosthesis 100 or otherwise in a utilitarian manner that will achieve a utilitarian result. This processed data is then transferred to the hearing prosthesis 100 via the link 230, thus communicating the results of the function of sound processing that would normally be executed by the hearing prosthesis 100 but in this instance is executed by the remote device 240 due to the migration of the functionality via the wireless link 230, and thus enabling the hearing prosthesis 100 to evoke a hearing percept via output 3246 to tissue of the recipient (where output 3246 corresponds to electrical stimulation in the case of the hearing prosthesis 100 being a cochlear implant, and output 3246 corresponds to vibrations in the case of a bone conduction device, etc.).

Accordingly, in view of the above, in an exemplary embodiment, one of the one or more functions is a first function corresponding to the processing of data based on sound captured by the hearing prosthesis, and the hearing prosthesis is configured to evoke a hearing percept based on communicated results of the first function from the remote device.

Still further, in an exemplary embodiment, the hearing prosthesis 100 is configured to transmit first data corresponding to transduced sound captured by the hearing prosthesis to the remote device (e.g., data corresponding to the raw output of the microphone of the external component of the hearing prosthesis), and the remote device is configured to receive the transmitted first data and process the first data into second data, the processing of the first data corresponding to at least one function performed by the remote device. The remote device is configured to transmit the second data (the processed sound—data corresponding to that which would result from the sound processing of sound in the hearing prosthesis 100) to the hearing prosthesis. The hearing prosthesis is configured to receive the second data transmitted from the remote device and evoke a hearing percept based on the received transmitted second data. In an exemplary embodiment, the hearing prosthesis 100 is configured to do all this in lieu of utilizing the onboard sound processor to process sound. Still further, in view of the above, it can be seen that the sound processing functionality migrated to the remote device duplicates the sound processing functionality of the hearing prosthesis. Thus, in an exemplary embodiment, the hearing prosthesis is configured to process the first data into third data in a manner at least substantially the same as (including the same as) that by which the remote device processes the first data into second data, and evoke a hearing percept based on the third data. In an exemplary embodiment, the system 100 is configured such that the processing of the first data into second data and third data is such that regardless of which data is utilized to evoke a hearing percept (second or third data), the objective quality of the evoked hearing percept is effectively indistinguishable.

Further to this end, in an exemplary embodiment, the system 210 is configured such that the remote device is configured to perform a sound capture function and substantially all processing functions of the hearing prosthesis. In this regard, for purposes of example and explanation, the portable handheld device 240, which can correspond to the remote device, can be considered to include a black box unit 342 with an input 344 and an output 346, as conceptually seen in FIG. 3B. Still further for purposes of discussion, hearing prosthesis 100 can be considered to have a black box unit 3142, such as depicted by way of example in FIG. 3C, having input 3144 and output 3146. In an exemplary embodiment, black box 342 is configured such that, providing that the input 344 corresponds to the input 3144, the black box 342 processes the input 344 in such a manner that the output 346 is substantially the same (including the same) as the output 3146 of the black box 3142. Thus, in an exemplary embodiment, where input 344 corresponds to, for example, ambient sound, and thus the black box 342 has the functionality of a sound capture device (e.g., microphone), along with processing functionality, the output 346 can corresponds to the output of a sound processor of the hearing prosthesis (e.g., output 3146), which output is utilized by a tissue stimulator to evoke a hearing percept. That said, in an alternative embodiment, the input 344 can be an output from a sound capture device, such as a microphone. That is, the black box 342 does not have the functionality of a sound capture device, but instead has only the functionality of a sound processor.

Figure 3D:
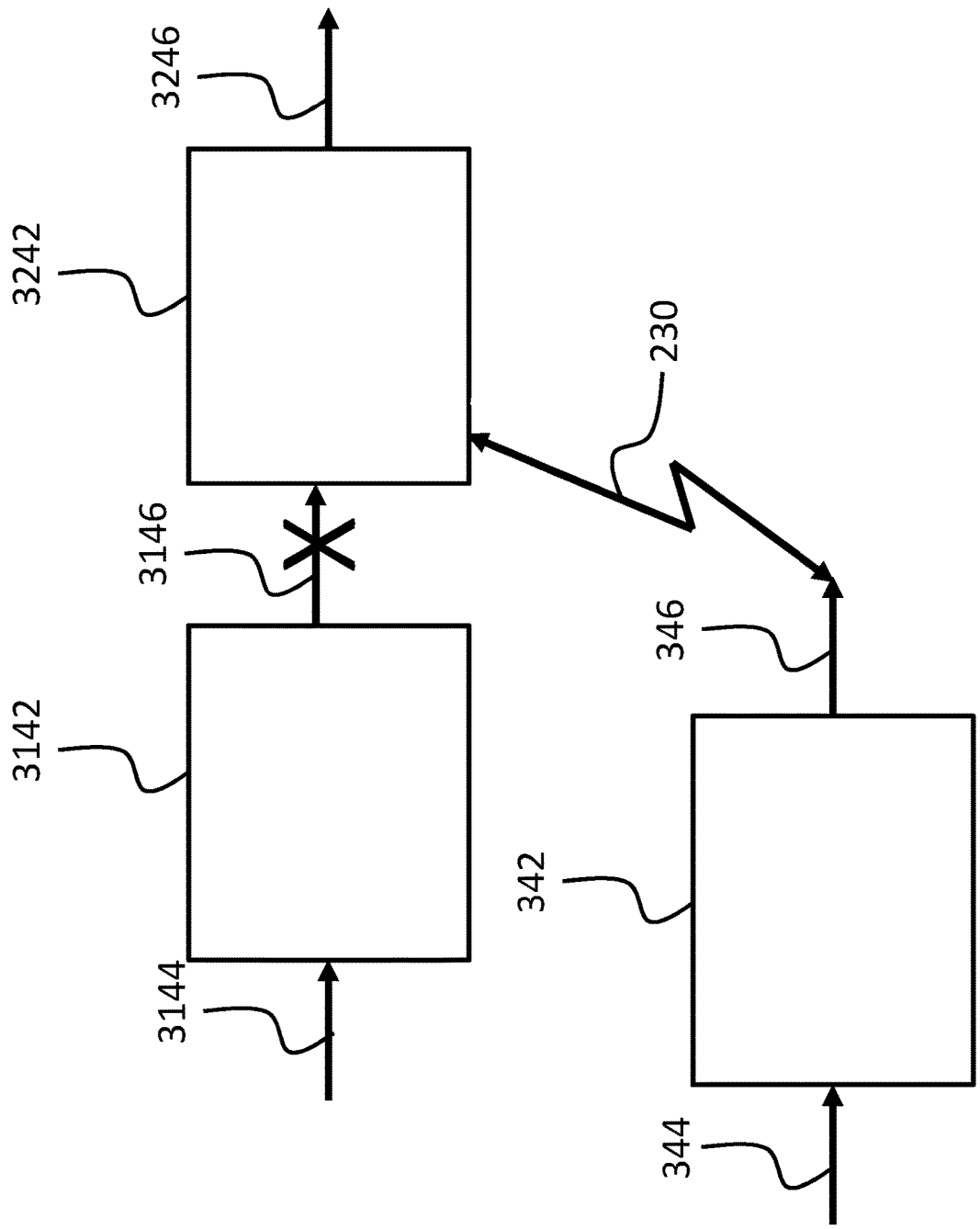
FIG. 3D presents an exemplary functional arrangement detailing communication between black boxes of the hearing prosthesis and a black box of the remote device.

Still further, in an exemplary embodiment, the hearing prosthesis 100 is configured to evoke a hearing percept based entirely on communications from the remote device (e.g., handheld device 240) of data (e.g., output 346) that is based on the result of performing sound capture by the remote device and performing substantially all processing functions of the hearing prosthesis by the remote device. That is, in this exemplary embodiment, the hearing prosthesis 100 is configured to use a signal based on output 346 from the remote device, which output can be wirelessly transmitted to the hearing prosthesis 100, as if the output 346 corresponded to output 3146. This is functionally represented by FIG. 3D, which depicts a second black box 3242 of the hearing prosthesis 100 corresponding to a tissue stimulator (e.g., a cochlear electrode array stimulator, or, for example, an actuator of a bone conduction device embodiments where the hearing prosthesis is a bone conduction device, etc.) and the associated components of the hearing prosthesis 100 that transmit data (e.g., a component of an external component that takes output 3146 and then transcutaneous transmits data based on output 3146—thus black box 3242 functionally represents components that are implanted in the recipient as well as components that are located external to the recipient), where output 3246 corresponds to output of the stimulator to stimulate tissue and thus evoke a hearing percept (e.g., electrical current in the case of a cochlear electrode array, vibrations in the case of a bone conduction device, etc.). Thus, in an exemplary embodiment, the hearing prosthesis 100 functions only to receive a signal based on the output 346 of device 342 via wireless link 230, and transmit data based on that signal to the tissue stimulator components of the hearing prosthesis to evoke a hearing percept based on the output 346 instead of the output 3146 (where there may be no output 3146 in a scenario where there is insufficient power supply to power black box 3142 and/or black box 3142 is not properly functioning etc., as represented by the "X" across output 3146). Thus, with reference to the above described configuration where the remote device is configured to perform a sound capture function and substantially all processing functions of the hearing prosthesis, all that the hearing prosthesis 100 is needed to do is to receive the output 346 from the remote device and transmit that output to the tissue stimulator (where substantially no processing (including no processing) is utilized to do such).

It is briefly noted that embodiments detailed herein refer to some components located on the external component of the hearing prosthesis. By way of example only and not by way of limitation, as detailed above, the sound processor of the hearing prosthesis is indicated as being located on the external component (e.g., BTE 126). It is noted that in other embodiments, the components referred to herein that are indicated as being located on the external component of the hearing prosthesis can alternatively be located in the implantable component (and vice versa). By way of example only and not by way of limitation, the aforementioned sound processor and/or the aforementioned microphone of the hearing prosthesis can be located on the implantable component of the hearing prosthesis, such as is the case in a totally implantable hearing prosthesis.

Still further by way of example, one of the one or more functions of the hearing prosthesis performed by the remote device, in lieu of the hearing prosthesis owing to migration, is a first function corresponding to a classification of sound based on sound captured by the hearing prosthesis. By way of example only and not by way of limitation, in at least some embodiments, the hearing prosthesis 100 is configured to classify sounds into different categories, such as background sound, speech, own voice, body conducted noise, etc. In an exemplary embodiment of this exemplary embodiment, the hearing prosthesis is configured to alter a processing of sound captured by the hearing prosthesis based on the first function. Accordingly, in this exemplary embodiment, the hearing prosthesis is configured to alter a processing of the sound based on classification of the sound done by the remote device (e.g. portable handheld device 240). By way of example only and not by way of limitation, such exemplary functionality can have utilitarian value in that a classification system of the hearing prosthesis will not require power, as it will not be utilized to classify sound, as such classification by the classification system by the hearing prosthesis is not needed because a classification system of the remote device is utilized to classify the sound. It is further noted that an exemplary embodiment of this embodiment can be implemented in a scenario where the remote device 240 is capturing the sound upon which the hearing percept is evoked by the hearing prosthesis 100, as well as in a scenario where the hearing prosthesis 100 is capturing the sound upon which the hearing percept is evoked and data based on the sound is transmitted to the remote device 240 such that the classification system thereof can be implemented.

Accordingly, in view of the above, in an exemplary embodiment, at least some of the functionality associated with noise management/noise cancellation, can be transferred from the hearing prosthesis 100 to the remote device 240. In an exemplary embodiment, the remote device 240 is configured such that the remote device can execute the functionality transferred thereto to obtain a result that is effectively the same as (including the same as) that which would be the case if the functionality was executed by the hearing prosthesis. Indeed, in at least some exemplary embodiments, the evoked hearing percept by the hearing prosthesis 100 is effectively identical (including identical) to that which would be the case if the functionality was executed by the hearing prosthesis, instead of executed by the remote device. In this regard, in an exemplary embodiment, the remote device 240 can include any or all of the algorithms that are contained in the hearing prosthesis 100, or otherwise be configured to utilize any or all of the algorithms that are utilized by the hearing prosthesis 100 to evoke a hearing percept (e.g., noise reduction algorithms, scene classifier algorithms etc.).

In view of the above, an exemplary algorithm usable by the system 210 to implement automatic migration/transfer of functionality from the hearing prosthesis 100 to the remote device 240 will now be described with reference to flowchart 400 of FIG. 4, where the functionality is an alert to the recipient that a given scenario has occurred. It is noted that the algorithm of flow chart 400 is but one exemplary algorithm that can be utilized with the system 210. Variations of this algorithm can be implemented in other embodiments. Indeed some exemplary variations will be described by way of example only, and not by way of limitation, in the following description of the algorithm of flow chart 400. To be clear, any device, system and/or method that can enable the teachings detailed herein to be practiced and/or variations thereof can be utilized in at least some embodiments.

Figure 4:
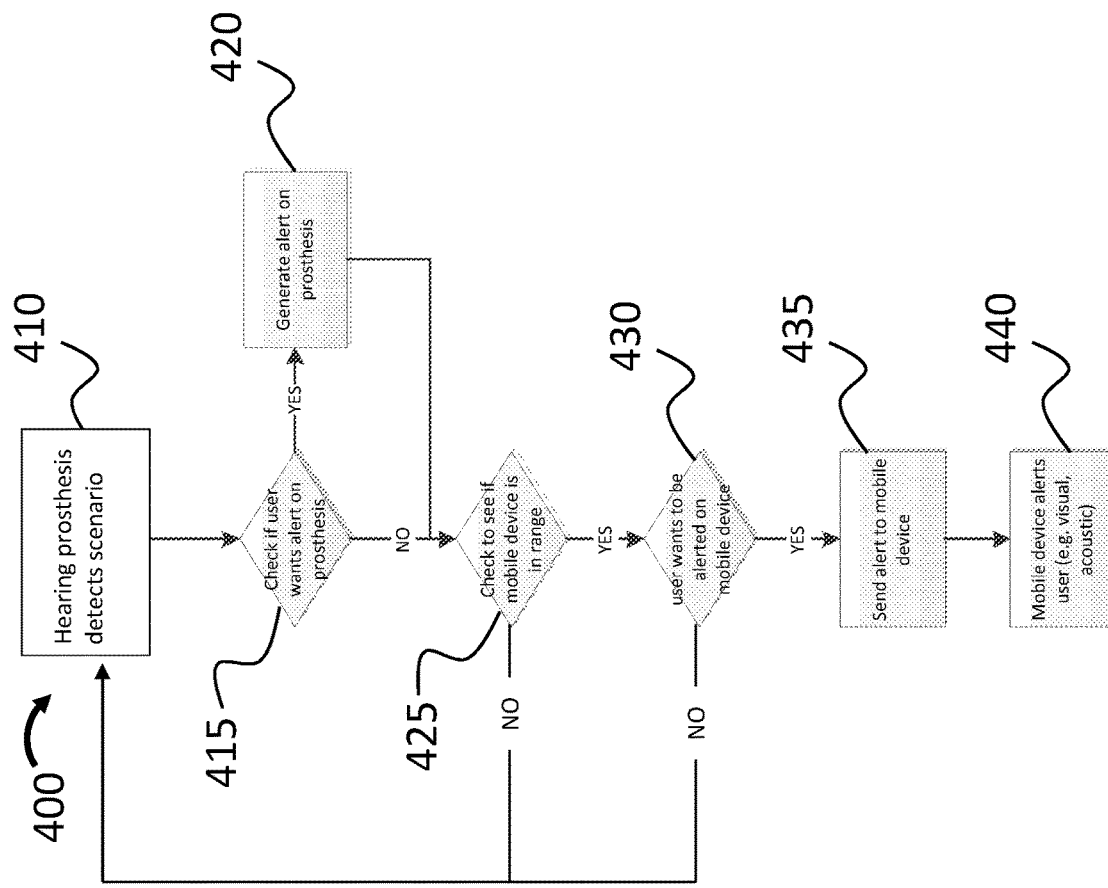
FIG. 4 presents an exemplary flowchart for an exemplary algorithm according to an exemplary embodiment.

Continuing with reference to FIG. 4, as can be seen, flow chart 400 begins with block 410, which entails the hearing prosthesis 100 detecting a scenario that warrants the triggering of alert according to at least one setting in the hearing prosthesis. By way of example only and not by way of limitation, the detected scenario could be a low battery level (e.g., the battery of the hearing prosthesis 400 is depleted to a predetermined level, such as, for example, 10% of capacity). Execution of the actions of block 410 can be performed via an internal algorithm of the hearing prosthesis that automatically performs a status check of various aspects of the hearing prosthesis according to a predetermined schedule (e.g., every 10 seconds, every minute, upon the implementation of a given setting by the user once or after a predetermined number of implantations, etc.). Flowchart 400 then moves to block 415, which entails the hearing prosthesis automatically checking to determine whether the user desires an alert from the hearing prosthesis 100. In this regard, as noted above, in an exemplary embodiment, the hearing prosthesis 100 can be configured such that the recipient can input a command into the hearing prosthesis 100 that will indicate whether or not the recipient wants the prosthesis to provide him or her an alert (enable the prosthesis to provide the alert/block the prosthesis from providing the alert). Corollary to this is that in an alternative embodiment, block 415 can be coupled with the action of the hearing prosthesis automatically checking whether or not it is capable of providing the alert and/or whether or not there is utilitarian value in instead of having the remote device 240 provide the alert. Regardless, upon a determination by the hearing prosthesis that the user wants an alert from the prosthesis, the algorithm proceeds to block 420, which entails generating alert on the prosthesis. By way of example only and not by way of limitation, this could be the activation of an LED. Alternatively and/or in addition to this, this could be the implementation of an evoked hearing percept of a beep or the like by the hearing prosthesis. Upon the completion of block 240, or alternatively, in the event that the check by the hearing prosthesis in block 415 yielded a no result, the algorithm proceeds to block 425, which entails the hearing prosthesis checking to see if the remote device 240 (mobile device in this exemplary scenario) is in wireless communication range with the hearing prosthesis 100 (e.g., the hearing prosthesis 100 can check to see if the link 230 is in existence, and if such link is indeed in existence, determined that the remote device 240 is in the range). If the check yields a no result, the algorithm returns back to block 410 to await the hearing prosthesis automatically detecting another scenario (which could be the continued presence of the scenario that initiated the algorithm in the first instance).

If the check at block 425 yields a yes result, the algorithm proceeds to block 430, which entails the hearing prosthesis 100 checking to see if the user desires to be alerted on the remote device 240 (mobile device). If the check yields a no result, the algorithm returns back to block 410 to again wait the hearing prosthesis automatically detecting another scenario. If the check at block 430 yields a yes result, the algorithm proceeds to block 435 which entails sending instructions to the remote device 240 via wireless link 230 to implement an alert to the recipient pertaining to the detected scenario. The algorithm then proceeds to block 440, which entails the remote device 240 alerting the recipient of the scenario (and thus implementing the functionality that was migrated from the hearing prosthesis). By way of example only and not by way of limitation, the action of block 440 can entail the remote device 240, which an exemplary embodiment is a smart phone as that term is used generically, displaying on the screen thereof a message to the recipient regarding the scenario (e.g. "prosthesis battery level low"). In an exemplary embodiment, this can be coupled with, for example, the remote device 240 beeping or vibrating, etc., or taking any other action that will alert the recipient that some form of message has been displayed on the remote device 240. Indeed in an exemplary embodiment, the remote device 240 can synthesize speech and state the alert using synthesized speech. Corollary to this is that in an exemplary embodiment, the remote device 240 is configured to receive the data transmission over link 230 from the hearing prosthesis regarding given scenario, and evaluate that data to determine which functionality of the hearing prosthesis should be implemented and thus implement that functionality. Alternatively and/or in addition to this, the hearing prosthesis can be configured to provide instructions to the remote device 240 to instruct the remote device which alert to display. That is, in an exemplary embodiment, the hearing prosthesis 100 can function as a master and the remote device 240 can function as a slave. This is opposed to the alternate embodiment where the hearing prosthesis 100 provides data to the remote device 240, and the remote device 240 analyzes that data and determines what action it should take. Any arrangement, including any devices, systems and/or methods that can enable the migration of the functionality to be executed can be utilized in at least some embodiments.

Briefly, it is noted that while block 425 is presented as being executed prior to block 430, in an alternative embodiment, block 430 can be executed prior to block 425. Indeed, in at least some exemplary embodiments, block 425 is not implemented. For example, irrespective of whether or not the remote device 240 is in range, the hearing prosthesis 100 can broadcast the data regarding the alert. If the remote device 240 is in range, the remote device can proceed accordingly. If not, the functionality is not migrated. Still further, in an exemplary embodiment, the hearing prosthesis 100 can be configured to perform a check to determine whether or not the functionality has been migrated. If a determination is made that functionality has not been migrated, the hearing prosthesis may give a warning to the recipient that the functionality was not migrated so that the recipient is aware that the functionality was not migrated and thus does not proceed or otherwise take actions upon the mistaken belief that functionality was migrated or otherwise will be migrated. Indeed, in an exemplary embodiment, even in a scenario where a trigger has not occurred that would migrate functionality, the hearing prosthesis 100 is configured to periodically check to determine whether or not functionality can be migrated, and upon a determination that the functionality cannot be migrated (e.g. for example, in the event that the hearing prosthesis 100 determines that the remote device 240 is not within range), the hearing prosthesis 100 provides a warning to the recipient that functionality will not be migrated. The warning can be a general warning that no functionality will be migrated, or, can be a specific warning about a specific functionality in a scenario where only some functionality can be migrated in some functionality cannot be migrated.

Figure 5:
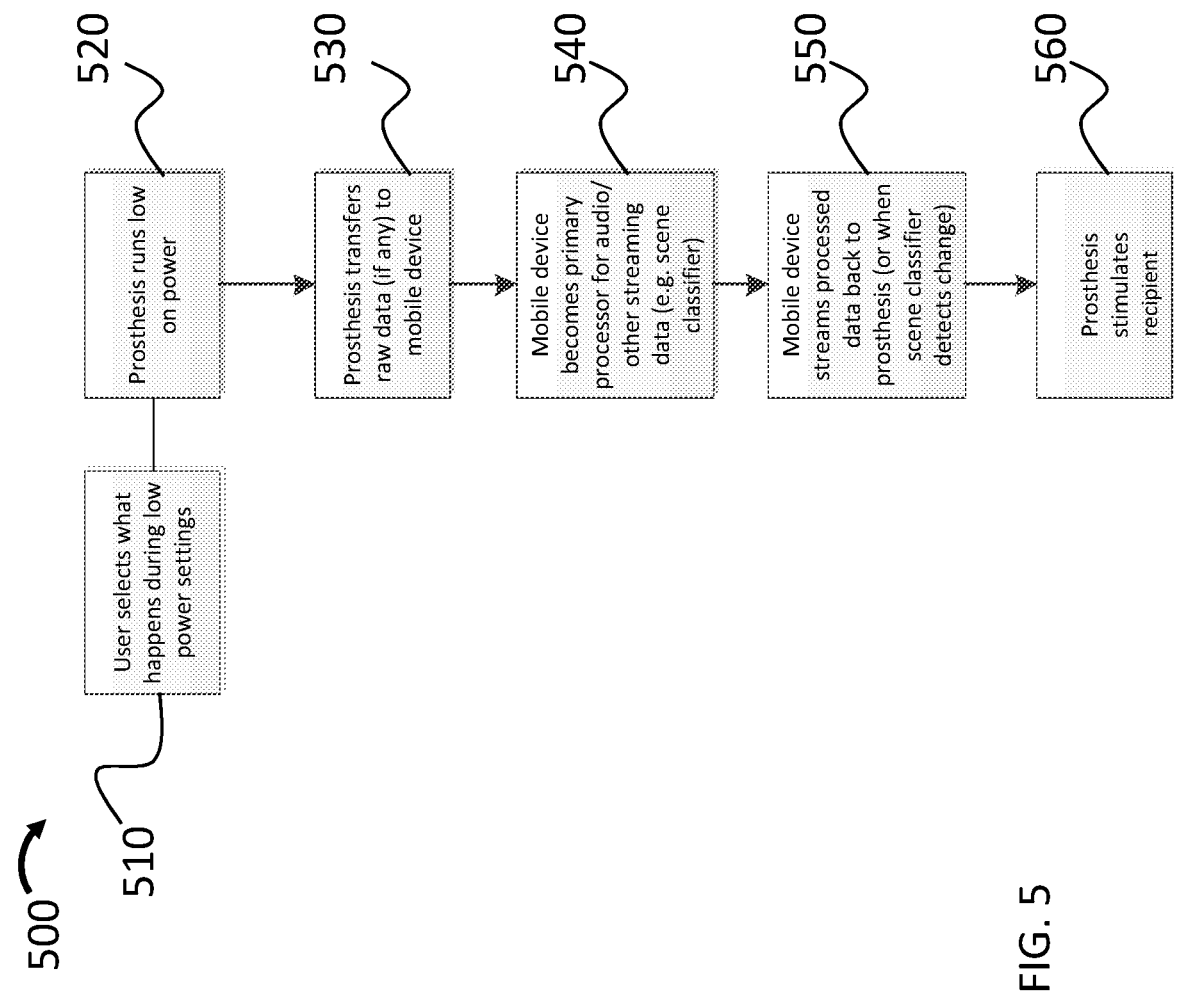
FIG. 5 presents another exemplary flowchart for another exemplary algorithm according to an exemplary embodiment.

Now with reference to the flow chart 500 of FIG. 5, an exemplary algorithm exists for utilization of the system 210 in a scenario where the hearing prosthesis runs low on power. (This is the exemplary algorithm noted above that exists for the utilization of the arrangement of FIG. 3A.) More specifically, at block 510 of flow chart 500, the recipient selects what is to happen during low-power scenarios afflicting the hearing prosthesis. By way of example, the recipient can select the sound processor functionality to be migrated to the remote device 240. At some time in the future after block 510 is executed, the algorithm proceeds to block 520, where the prosthesis runs low on power. In an exemplary embodiment, this crisis is detected by a battery management system of the hearing prosthesis 100. Upon the determination at block 520 that the hearing prosthesis is running low on power, the algorithm proceeds to block 530, where the hearing prosthesis 100 automatically migrates the functionality of sound processing from the hearing prosthesis 100 to the remote device 240. This method action is exemplified by the hearing prosthesis 100 disabling the sound processor thereof and beginning to transfer the raw data outputted by the microphone of the hearing prosthesis 100 (if present—if there is no ambient sound, the microphone might not have any output) to the remote device 240 via link 230. It is noted that in an alternative embodiment, prior to the execution of block 530, the hearing prosthesis 100 performs automatic determination as to whether or not there exists a power savings and/or a significant power savings by proceeding to block 540. By way of example only and not by way of limitation, a scenario may exist where transmitting raw data to the remote device 240 (mobile device in this example) is more power intensive than continuing to utilize the sound processor of the hearing prosthesis 100 without the raw data transmission. If a determination is made that the difference in power consumption by proceeding to block 540 is not utilitarian, the algorithm can stop here (not proceed further) in some instances. That said, if there is no such management feature enabled, or there is otherwise a determination that there will be utilitarian power savings by proceeding to block 540, the algorithm then proceeds to block 540, where the remote device 240 becomes the primary processor for the audio data and/or for any other streaming data that may be present, thus averting or otherwise mitigating the crisis of low power of the hearing prosthesis (e.g., by prolonging the length of time that the hearing prosthesis 100 can evoke a hearing percept, albeit based on process data from the remote device 240). As noted above, in an exemplary embodiment, one of the migrated functionalities can be a scene classifier functionality. Accordingly, alternatively and/or in addition to the remote device 240 having the functionality of the sound processor, the remote device 240 can have the functionality of the scene classifier.

The algorithm then proceeds to block 550, where the remote device 240 (mobile device in this example) streams processed sound data back to the hearing prosthesis 100 via wireless link 230. Alternatively and/or in addition to this, in the case of the remote device having the functionality of the scene classifier, the remote device 240 provides data via link 230 to the hearing prosthesis 100 indicating that the scene classification has changed and/or detailing the status of the new scene classification. The algorithm then proceeds to block 560, where the hearing prosthesis stimulates tissue of the recipient to evoke a hearing percept based on the data transmitted from the remote device 240 to the hearing prosthesis 100.

It is noted that these algorithms are but exemplary algorithms for exemplary migrated functionalities. Other embodiments can use other algorithms, including variations of these algorithms, for other migrated functionalities and for the same migrated functionalities. Any algorithm that can enable the teachings detailed herein and/or variations thereof to be practiced can be utilized in at least some embodiments, at least providing that such can have utilitarian value with respect to doing so.

In view of some of the above examples, it is to be understood that functionality migration need not necessarily correspond to situations where the result will have a one-to-one relationship with the functionality of the hearing prosthesis if executed thereby. By way of example only and not by way of limitation, in an exemplary embodiment, the hearing prosthesis can be configured to automatically wirelessly communicate data based on captured speech to the remote device upon an automatic determination by the hearing prosthesis that the hearing prosthesis cannot evoke a hearing percept based on the captured speech. This can be, for example, in a scenario where the transcutaneous link between the external component and the implantable component of a cochlear implant has failed, and thus it is impossible to evoke a hearing percept. In this exemplary embodiment, the remote device 240, which is configured to automatically display text corresponding to a speech content of the captured speech wirelessly communicated to the remote device by the hearing prosthesis, automatically so displays the text. Accordingly, the functionality of conveying to the recipient the content of audible words present in the ambient sound is migrated from the hearing prosthesis to the remote device 240, albeit the functionality is achieved in a different manner (instead of evoking a hearing percept, text is displayed).

Is also noted that in at least some exemplary embodiments, the system 210 is configured such that the basic functionality of the hearing prosthesis is migrated to the remote device 240 in some instances. Indeed, in an exemplary embodiment, the system 210 is configured to migrate all functionalities of the hearing prosthesis to the remote device 240, including but not necessarily, all processing functions and/or all non-processing functions. By way of example only and not by way of limitation, the system 210 is configured to shut down the hearing prosthesis entirely, and instruct the remote device 240 to capture sound, process the sound, and display text based on the sound in scenarios where the sound includes spoken words. Still further, by way of example only and not by way of limitation, the system 210 is configured to shut down all but the sound capture functionality of the hearing prosthesis 100 and the data transmission functionality the hearing prosthesis 100, and have the hearing prosthesis 100 transmit data based on the captured sound via wireless link 230 to the remote device 240, where the remote device displays text based on spoken words of sound captured by the hearing prosthesis 100. Corollary to the above is that in at least some embodiments, the hearing prosthesis 100 is configured to automatically transfer or otherwise migrate functionality such that the remaining power can be devoted to the core functions of the hearing prosthesis 100, and all other remaining functionalities are either performed by the remote device 240 or not performed at all.

It is noted that while features of the remote device 240 have been described in some instances above, the teachings of the above have been primarily directed towards features of the hearing prosthesis 100. It is noted that in at least some exemplary embodiments, one or more or all of the functionalities of the hearing prosthesis 100 detailed above can be, in at least some embodiments, the functionalities that can be migrated to the remote device 240. Corollary to that is in at least these embodiments, the remote device 240 is configured to have the functionality (or at least simulate the functionality—more on this below) of the hearing prosthesis that is migrated.

Some exemplary embodiments will now be detailed with respect to embodiments of the system 210 having functionalities of the remote device 240 migrated to the hearing prosthesis 100. In this regard, it is noted that any disclosure of the migration of a functionality from the hearing prosthesis to the remote device corresponds to a disclosure of a migration of that functionality from the remote device to the hearing prosthesis, providing that such embodiments have that functionality on the remote device or otherwise have the ability to replicate that functionality in the first instance. Still further, it is noted that any disclosure of the migration of a functionality from the remote device to the hearing prosthesis corresponds to a disclosure of a migration of that functionality from the hearing prosthesis to the remote device, providing that such embodiments have the functionality on the hearing prosthesis in the first instance.

Concentrating now on migration of functionality from the remote device 240 to the hearing prosthesis 100, some exemplary embodiments of such will now be described.

Figure 6:
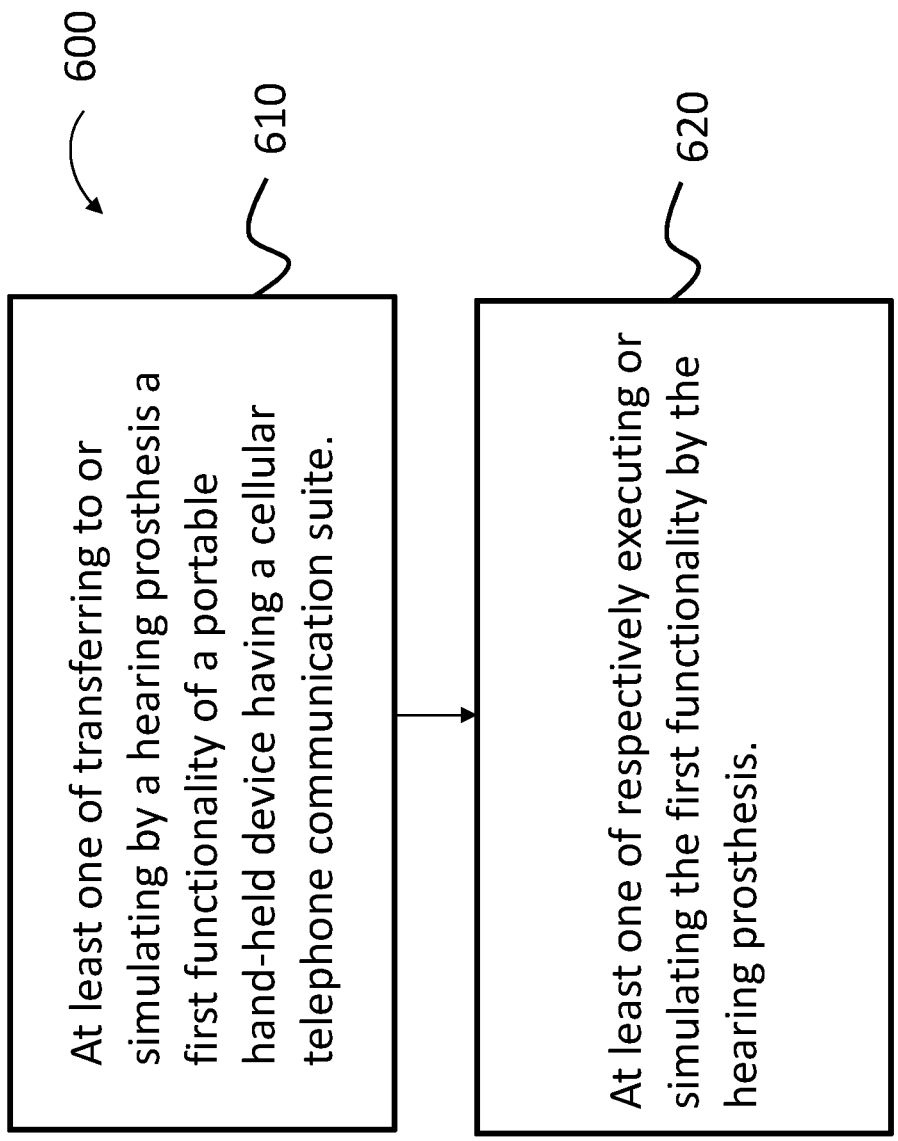
FIG. 6 presents another exemplary flowchart for another exemplary algorithm according to an exemplary embodiment.

Referring now to FIG. 6, there is an exemplary flow chart 600 that provides an exemplary method according to an exemplary embodiment. Specifically, the method of flow chart 600 begins with method action 610, which entails at least one of transferring to or simulating by a hearing prosthesis a first functionality of a portable handheld device having a cellular telephone communication suite (e.g., a smart phone as that term is used generically). In an exemplary embodiment, for the purposes of the exemplary illustration only, this first functionality is the functionality of a calendar based reminder of a teleconference in which the recipient must participate (e.g., in the exemplary embodiment utilizing the generic smart phone, where the recipient has inputted a calendar reminder into the calendar thereof, the generic smart phone will normally provide an indication of the recipient that the meeting will commence within a given period of time (along with, for example, a vibratory indication to prompt the recipient to look at his or her smart phone)).

In an exemplary embodiment, the transferring action of 610 can be initiated by the recipient. Alternatively, it can be an automatic transfer initiated by some triggering event (e.g., the smart phone running low on power—more on this below). Flow chart 600 further includes method action 620, which entails at least one of respectively executing or simulating the first functionality by the hearing prosthesis. In an exemplary embodiment, the hearing prosthesis has an onboard timer or the like, and provides a reminder to the recipient of the upcoming teleconference (e.g., the hearing prosthesis can evoke a hearing percept corresponding to simulated speech stating that the teleconference begins in a given temporal period).

It is noted that the method of flow chart 600 refers to both transferring and simulating functionality. In the just described example, where the hearing prosthesis 100 includes a timer, the functionality of the remote device 240 is indeed transferred. In this regard, the hearing prosthesis 100 can perform autonomously without the remote device 240 being activated (at least after the functionality has been transferred, along with any data required to execute the functionality (e.g., a time in which the meeting begins)). Conversely, the hearing prosthesis 100 may not necessarily include a timer. Instead, the remote device 240 is configured to provide a signal to the hearing prosthesis 100 at a specific time according to the calendar to prompt the hearing prosthesis 100 to remind the recipient of the upcoming meeting. In this regard, the functionality of the remote device 240 (in this case, the calendar) is simulated by the hearing prosthesis 100. That is, the hearing prosthesis 100 does not have the functionality of the remote device 240 with regard to a timer or the like, but the functionality of the timer is simulated thereby. (It is noted that an exemplary functionality can also be simulated by the remote device 240 in some alternate embodiments, instead of executing a given functionality.)

Accordingly, in view of the above, in an exemplary embodiment, an alarm (in the concept of an alarm of an alarm clock) set on a cell phone or the like (corresponding to portable handheld device 240 of system 210) can be transferred to the hearing prosthesis 100 so that the recipient receives the alarm at the appropriate time. In the case of transferring the functionality, the data associated with the temporal features of the alarm is transferred from the cell phone after it is inputted therein by the recipient (pre-migration synchronization, as further detailed below), and the hearing prosthesis 100 utilizes that data with its own internal calendar system to initiate the alarm at the appropriate time. In the case of simulating the functionality, the cell phone utilizes its own internal calendar, and at the appropriate time, sends a signal to the hearing prosthesis 100, which provides the alarm to the recipient, thus simulating the functionality of the alarm feature of the cell phone.

It is noted that not only the temporal data can be transferred to the hearing prosthesis, but other facets of the alarm can be transferred to the hearing prosthesis, such as by way of example only and not by way of limitation, data about the alarm, such as the type of ring tone that is desired, can be transferred to the hearing prosthesis (different ring tones for different people/telephone originating numbers can be utilized by the remote device 240, and thus the different ring tones can be presented to the recipient when the functionality is transferred and/or simulated by the hearing prosthesis).

Accordingly, in view of the above, in an exemplary embodiment, the transferred first functionality (with reference to the above) is a temporally-based notification to a recipient, and the execution of the first functionality by the hearing prosthesis is automatic and includes notifying the recipient that a temporal-based event at least one of has happened or will happen.

Figure 7:
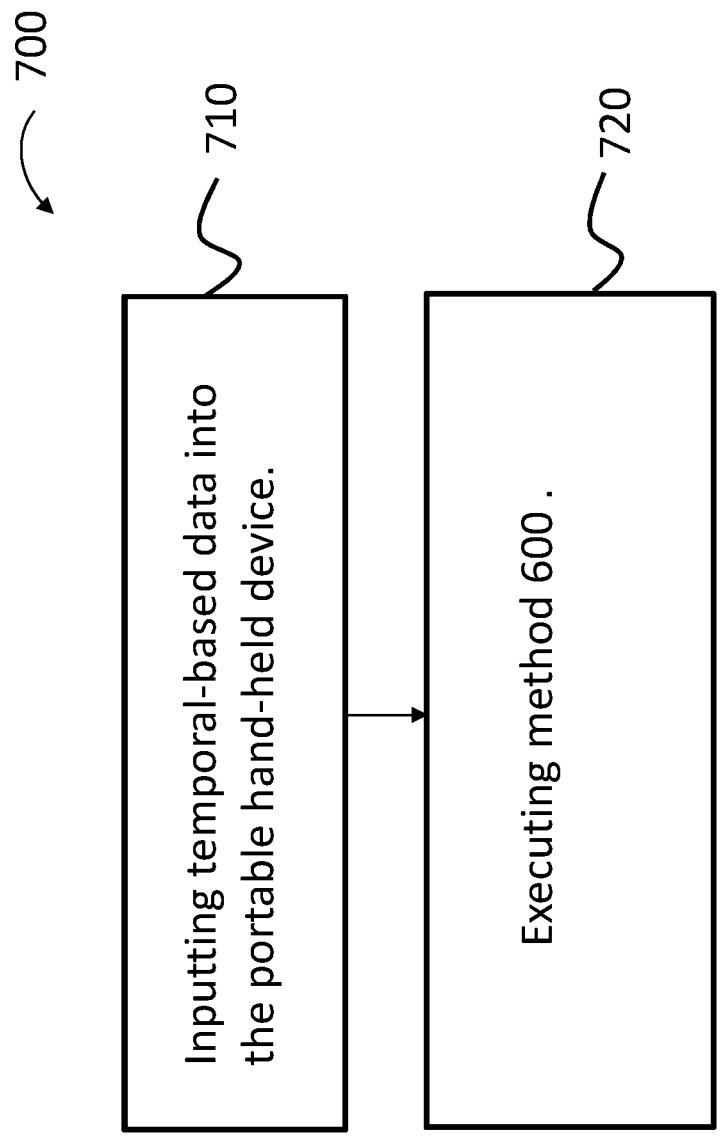
FIG. 7 presents another exemplary flowchart for another exemplary algorithm according to an exemplary embodiment.

In some exemplary embodiments of system 210, there is a pre-migration process that takes place. In this regard, referring now to FIG. 7, there is an exemplary method according to flow chart 700, which entails method action 710, which entails the recipient inputting temporal-based data into the portable handheld device 240. The method of flow chart 700 proceeds to method action 720, which entails executing method 600 of FIG. 6. It is noted that in an exemplary embodiment, the method further comprises synchronizing the portable hand-held device with the hearing prosthesis by uploading the inputted temporally-based data to the hearing prosthesis (e.g., via link 230). This synchronization can be executed either before method action 600 is executed, or can be executed along with method 600 (e.g., it can be part of the action of transferring to the hearing prosthesis the first functionality (method action 610).

It is noted that in an exemplary embodiment, the action of synchronizing the portable hand-held device is executed automatically based on at least one of a predetermined temporally-based schedule or a predetermined event. By way of example only and not by way of limitation, the synchronization can occur every time data related to the migrated functionality is inputted into the remote device 240 (e.g., each time an alarm is set in the remote device 240, each time the hearing prosthesis is activated, each time the remote device 240 is brought into contact via link 230 with the hearing prosthesis, etc.). Alternatively and/or in addition to this, the synchronization can occur according to a periodic schedule (e.g., every 10 minutes, every hour, etc.). In an exemplary embodiment, the synchronization can occur based on a schedule set by the recipient. Still further, the synchronization can occur as a result of an input by the recipient/user to so execute the synchronization Corollary to the above, in an exemplary embodiment, the system 210 is configured such that the components thereof and/or the recipient thereof can control which applications/functions, datasets, etc. will migrate and/or when such migration will occur. In this regard, by way of example only and not by way of limitation, the remote device 240 can be configured with an app that enables the recipient to input information associated with the types of migrations and/or temporal details associated with a given migration. In this regard, in an exemplary embodiment, the remote device 240 can be configured to provide a list of questions or the like to the recipient via, for example, the display screen, which questions correspond to potential functions that can be migrated and/or when such migration shall occur (i.e., what triggers the migration). In at least some exemplary embodiments, the system 210 is configured to determine what pre-migration data must be synchronized with the various components, and automatically synchronize such (e.g., based on a schedule, based on the fact that the recipient has determined that a given function will be migrated, etc.).

An exemplary embodiment entails transferring functionality from the portable device 240 to achieve a hands-free and/or an eyes-free mode. By way of example only and not by way of limitation, the remote device 240 has the functionality of displaying data and/or messages and/or warnings on a screen thereof (e.g., email, text messages, graphics linked in the pertinent culture with some calamity, etc.). In an exemplary embodiment, the hearing prosthesis 100 is configured to simulate the display data. Thus, referring to the aforementioned first functionality detailed above, in an exemplary embodiment, the first functionality is a display of a received text based message, and in an exemplary embodiment the hearing prosthesis 100 stimulates the display of the text based message by evoking a hearing percept that is perceived by the recipient as language corresponding to the words of the text of the text based message. It is to be understood that in scenarios where the visual alarm of the remote device 240 is not text based, or even if it is text based, other types of prompts by the hearing prosthesis in addition to evoking a hearing percept indicative of speech can be utilized by the hearing prosthesis to simulate the functionality.

An exemplary embodiment of the functionality that can be migrated to the hearing prosthesis 100 entails, by way of example, input monitoring. For example, the hearing prosthesis 100 can be configured to log data in the event that the remote device 240 is absent or otherwise not in communication with the hearing prosthesis 100.

It is noted that in an exemplary embodiment, the above can have utilitarian value in that in some instances, only the recipient of the hearing prosthesis 100 can hear or otherwise know that the recipient is utilizing or otherwise receiving information from the remote device 240 (e.g., because the hearing percept evoked by the prosthesis 100 cannot be heard by anyone else, at least in the case of a cochlear implant). In this regard, in an exemplary embodiment, the action of respectively executing or simulating the first functionality by the hearing prosthesis is executed such that an active observer of the recipient corresponding to a human factors engineering 50 percentile 25 year old female citizen of the United States (i.e., a female citizen of the United States having physical and mental characteristics of the average 25 year old citizen) cannot recognize that the action has taken place in a non-tactile based manner (e.g., cannot recognize that the hearing prosthesis 100 has provided the recipient with the information that would otherwise be provided on the text screen of the remote device 240). The tactile based manner encompasses a scenario where, for example, the hearing prosthesis 100 is a bone conduction device. In this regard, an observer might be able to determine that the recipient has received information by touching the recipient in a manner that vibrations generated by the bone conduction device are transferred to the recipient.

Still further, such can have utilitarian value in scenarios where reading or otherwise viewing the remote device 240 is not possible and/or is not permitted and/or is not advantageous (e.g., while driving, while running across a street with heavy traffic, while taking an examination, when the recipient is exposed to bright sunlight, the recipient is temporarily blinded due to a flash, the recipient's vision is impaired because he or she has lost his or her set of glasses, etc.).

It is noted that in some embodiments of the hands-free/eyes-free mobile device mode, there is a method that entails developing data utilizing a functionality of the portable handheld device 240 that is migrated or otherwise transferred to the hearing prosthesis 100, and then entailing transferring that data back to the portable handheld device for further processing and/or further use. For example, in an exemplary embodiment, the first functionality is a smart phone functionality (as that term is utilized generically). In an exemplary embodiment, an exemplary method action includes transferring to the handheld device data developed as a result of the execution or simulation of the first functionality by the hearing prosthesis 100. For example, in an exemplary embodiment, the smart phone functionality is a voice-based functionality and the execution of the first functionality with the handheld device entails executing the voice-based functionality. In an exemplary embodiment, this can be voice-to-text functionality (where the functionality of the portable handheld device 240 enables the recipient to speak into a microphone thereof where the portable handheld device 240 converts the captured speech into text). Thus, in an exemplary embodiment, the hearing prosthesis 100 is configured such that the recipient can speak (e.g., talk to himself or herself) in such a manner that the microphone of the hearing prosthesis 100 picks up the speech of the recipient, and converts that speech to a dataset that is representative of text (or, in an alternative embodiment, where the portable handheld device 240 is being used as a voice recorder, record the sound of the recipient's voice, and thus record the words spoken thereby). Thus, the text developed by the hearing prosthesis 100, as a result of the migration of the functionality from the portable handheld device 240, corresponds to the aforementioned data developed as a result of the execution or simulation of the first functionality. As noted above, this data is transferred to the portable hand-held device 240. In this exemplary method, the method can further include the exemplary action of executing the first functionality (i.e., the functionality of the portable handheld device that was migrated to the hearing prosthesis 100) with the portable handheld device based on this transfer data. With regard to the current example, the data representative of text can be converted to text that is indeed displayed on the display of the portable handheld device 240.

In view of the above, it can be seen that an exemplary functionality that can be migrated to the hearing prosthesis 100, can be a smart phone functionality in the form of voice-based functionality, and the action of executing the first functionality with the hand-held device entails executing the voice based functionality after the data is transferred to the hand-held device.

In view of the above, an exemplary algorithm usable by the system 210 to implement automatic migration/transfer of functionality from the remote device 240 to the hearing prosthesis 100 will now be described with reference to flowchart 800 of FIG. 8, where the functionality is an alert that a meeting is to take place in the near future. It is noted that the algorithm of flow chart 800 is but one exemplary algorithm that can be utilized with the system 210. Variations of this algorithm can be implemented in other embodiments. Indeed, some exemplary variations will be described by way of example only and not by way of limitation in the following description of the algorithm of flow chart 800. To be clear, any device, system and/or method that can enable the teachings detailed herein to be practiced and/or variations thereof can be utilized in at least some embodiments.

Figure 8:
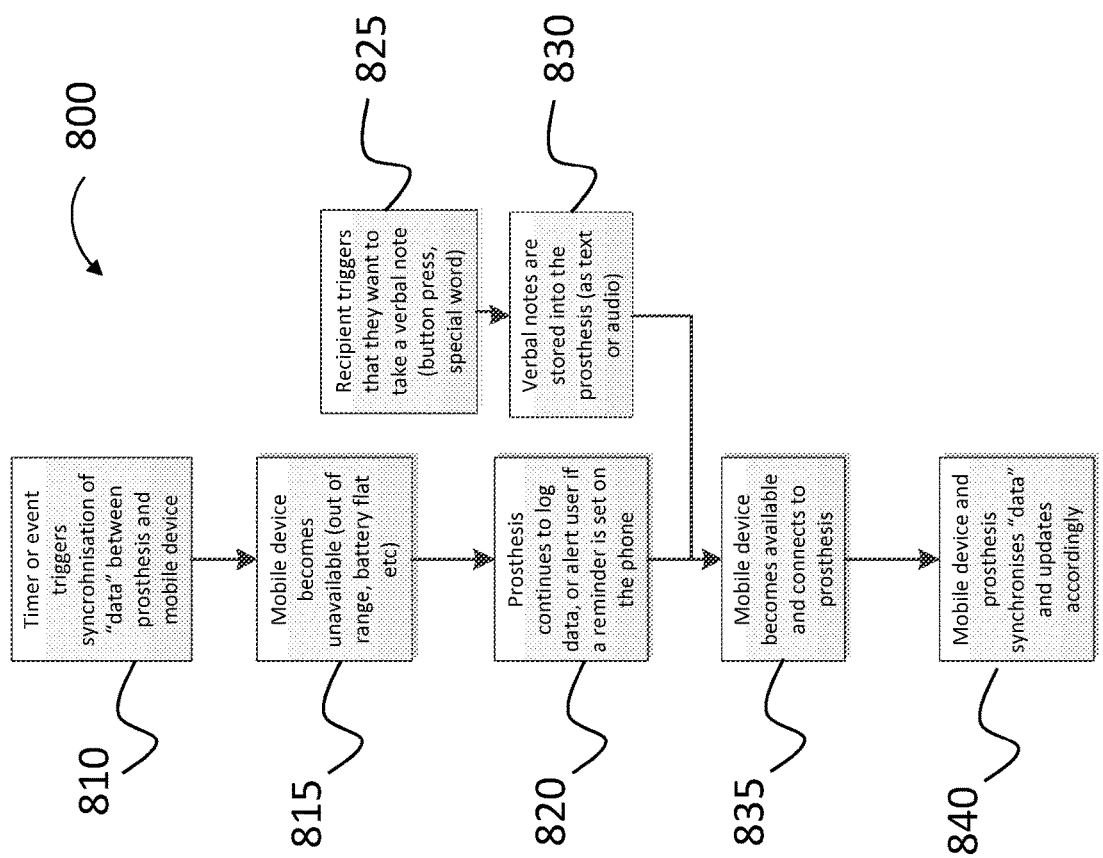
FIG. 8 presents another exemplary flowchart for another exemplary algorithm according to an exemplary embodiment.

Continuing with reference to FIG. 8, as can be seen, flow chart 800 begins with block 810, which entails a component of the system 210 (e.g., the hearing prosthesis 100 and/or the remote device 240) determining that a scenario has occurred that warrants the synchronization of data between the prosthesis and the remote device 240 (mobile device in this scenario). By way of example only and not by way of limitation, in an exemplary embodiment, this entails the establishment (including reestablishment) of wireless link 230 between the remote device 240 and the hearing prosthesis 100. Alternatively and/or in addition to this, this can entail a determination that the recipient has just activated the remote device 240 (e.g., powered up the remote device, taken the remote device out of airplane mode, etc.). In this exemplary embodiment, the synchronization entails the synchronization of data relating to a calendar function stored on the remote device 240. For example, that the recipient is to participate in a teleconference at 2:30 PM. Continuing with the flow chart 800, after the synchronization of block 810, the system 210 is utilized (the hearing prosthesis 100 is utilized to evoke a hearing percept based on, for example, speech of someone speaking to the recipient, and the remote device 240 is utilized to for example, read text messages). At some point after block 810, an event occurs that triggers a migration. In this regard, block 815 details that the remote device becomes unavailable for whatever reason (e.g., remote device 240 becomes out of range, becomes low on battery power, is shut off, etc.). At block 815, the functionality is migrated automatically from the remote device 240 to the hearing prosthesis. Flowchart 800 then proceeds to block 820, in which the prosthesis performs the functionality that was migrated thereto at block 815. In this exemplary embodiment, the functionality is provide a reminder/alarm to the recipient reminding the recipient that it is now 2:30 PM and the recipient must participate in the teleconference. It is noted that while this functionality results in, when residing in the remote device 240, a text message and/or a vibratory action and/or a tone, this functionality can result in a hearing percept of an artificial voice stating in a language that it is time to put us patent teleconference as a result of the migration of this functionality to the hearing prosthesis 100.

Still continuing with flowchart 800, at some point after block 820, the remote device 240 becomes available again and a connection is established between the remote device 240 and the hearing prosthesis 100 via the wireless connection 230 (as is represented by block 835 in FIG. 8). At some point after this connection is established, at block 840, the remote device 240 and the hearing prosthesis 100 synchronize with each other and update their data accordingly to achieve a utilitarian result. By way of example only and not by way of limitation, with respect to the aforementioned example, the hearing prosthesis number 100 could provide synchronization data to the remote device 240 detailing that the reminder about the teleconference has been provided to the recipient, and thus the remote device 240 clears that reminder from its system.

Still with reference to FIG. 8, it is noted that there is a branch to the flowchart 800 including blocks 825 and 830. In this regard, block 825 entails the recipient providing input to the hearing prosthesis 100 that he or she seeks to take a verbal note. Because the remote device 240 is unavailable as a result of block 815, the functionality of the verbal note feature of the remote device 240 has been migrated to the hearing prosthesis 100. Thus, the hearing procedures 100 performs this functionality upon the recipient providing the input thereto. After this, at block 830, the verbal note is stored in the prosthesis, as a text and/or an audio note. Flowchart 800 then proceeds to block 835, where the remote device 240 becomes available and connects to the prosthesis, as noted above, followed by block 840 where the mobile device in the prosthesis synchronize. In this exemplary branch scenario, the hearing prosthesis 100 downloads the data based on the verbal note (text file, audio file, etc.) to the remote device 240, and this verbal note is stored in the remote device 240 as if it was initially directly inputted therein by the recipient.

Figure 10:
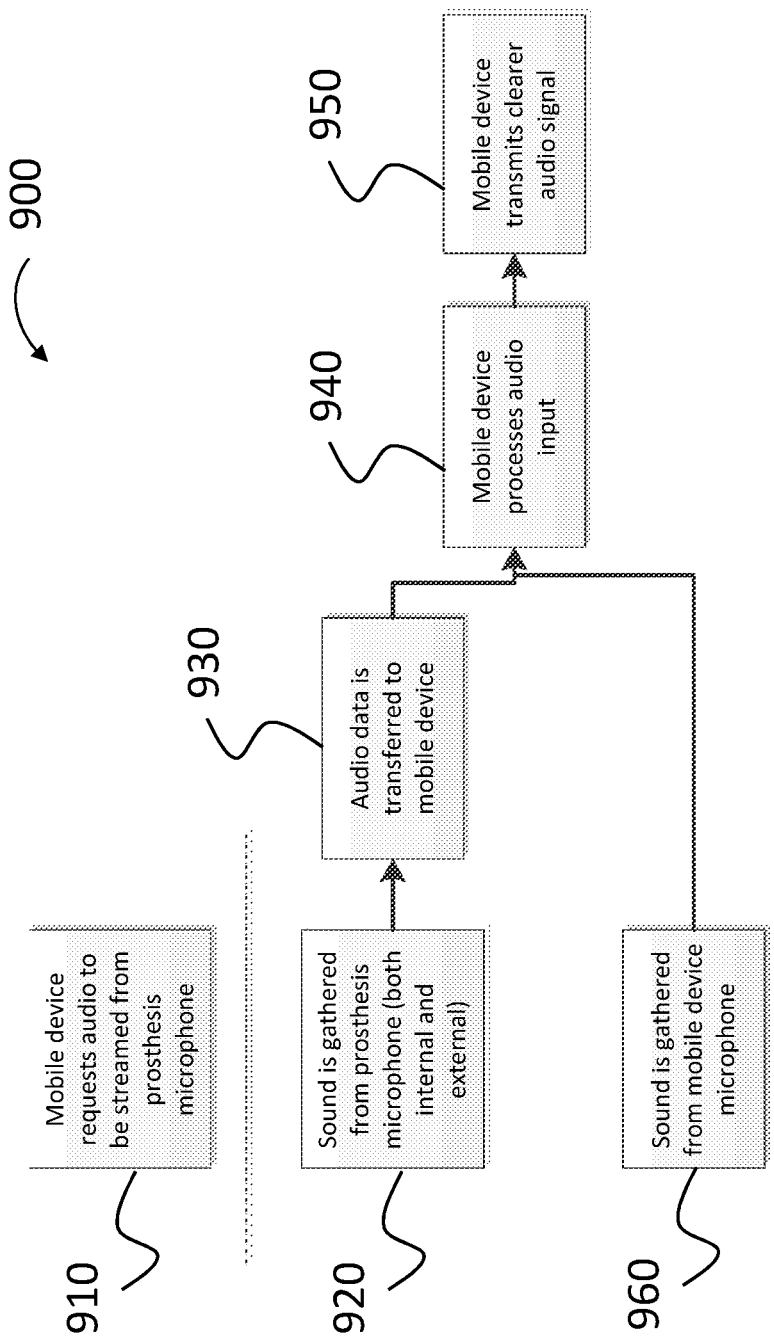
FIG. 10 presents another exemplary flowchart for another exemplary algorithm according to an exemplary embodiment.

Referring now to FIG. 10, there is an exemplary flow chart 900 detailing an exemplary scenario where functionality is transferred in real time from the remote device 240 to the hearing prosthesis for use by the remote device 240. More specifically, at block 910, the remote device 240, which in this exemplary embodiment is a mobile device, such as by way of example only and not by way of limitation, a cellular phone, determines that, for whatever reason, it cannot pick up sound utilizing it is microphone (e.g., sound as would be utilized to make a verbal note, sound to make a telephone call, etc.). At block 910, the remote device 240 request audio to be streamed from the hearing prosthesis 100. In this regard, the hearing prosthesis 100 includes a microphone which captures sound, and the sound captured thereby is deemed usable with respect to the functions associated with the remote device 240 that requires the input from the microphone of the remote device 240. Accordingly, at block 920, sound is gathered from the hearing prosthesis microphone, whether that microphone be a microphone on an external component or a microphone that is internal to the recipient (implanted). At block 930, the audio data resulting from the sound capture of the microphone of the hearing prosthesis is transferred to the remote device 240. In an exemplary embodiment, this is achieved via the wireless link 230. At block 940, the remote device 240 processes this audio input as if the audio input were from the microphone of the remote device 240, and at block 950, the remote device 240 utilizes this audio input for specific functionality thereof, such as by way of example only and not by way of limitation by transmitting a clearer audio signal in the case where the recipient is engaged in a cellular telephone conversation.

As can be seen, flowchart 900 includes a branch that includes block 960. In this exemplary alternative path, sound can still be gathered by the microphone of the remote device 240, utilizing the microphone thereof. In this regard, the method associated with flowchart 900 need not necessarily be implemented in the scenario where the microphone of the remote device 240 is completely useless. Instead, the method of flowchart 900 can be implemented in a scenario where the system 210 evaluates which is the better audio signal (the signal that is streamed from the hearing prosthesis 100 based on the microphone thereof versus the signal that is streamed from the microphone of the remote device 240). The system can determine which is the better audio signal prior to block 940, and execute block 940 utilizing the better audio signal. In this regard, by way of example only and not by way of limitation, the sound capture functionality can be migrated from the hearing prosthesis 100 to the remote device 240 automatically based on a trigger event corresponding to a determination that the audio signal based on the microphone of the hearing prosthesis 100 is more utilitarian than that based on the microphone of the remote device 240. Corollary to this is that a subsequent triggering event can entail transferring the sound capture functionality back to the remote device 240 upon a determination that the audio signal from the microphone of the remote device 240 has more utilitarian value than that of the hearing prosthesis 100.

As noted above, the method of flowchart 900 entails real time transfer of functionality/migration of functionality. Accordingly, in an exemplary embodiment, the system 210 is configured to automatically detect a trigger that will transfer the functionality in real time. Application of such real-time transfer of functionality/migration of functionality can include, by way of example only and not by way of limitation application during a cellular telephone call, during the action of executing dictation and/or the taking of notes utilizing a component of the system 210, and/or otherwise recording and events utilizing the system 210.

In view of the above, in at least some exemplary embodiments, a wide variety of the functionalities of a smart phone, as that term is utilized in the generic sense, can be migrated to the hearing prosthesis 100. In addition to the various discrete/hands free phone modes detailed above (e.g., where the recipient speaks messages, notes, reminders, phone numbers, etc., to themselves, where the hearing prosthesis 100 stores the captured spoken words of the recipient, or stores data based on the captured spoken word to the recipient, which is later downloaded to the smart phone utilize thereby just as if it was spoken to the smart phone by the recipient), the hearing prosthesis may perform other functionalities of the smart phone. By way of example only and not by way of limitation, in an exemplary embodiment, the functionality of a calculator can be migrated. Still further by way of example, a clock functionality could be migrated (e.g. where the hearing prosthesis 100 notifies the recipients of the time on the hour and/or on the minute and/or on the 5 minutes etc.).

Such functionality migration from the remote device 240 to the hearing prosthesis can have utilitarian value in situations where, for example, for whatever reason, the recipient cannot utilize the remote device 240 (such scenario being an automatic triggering event in at least some embodiments, at least where the system 210 is configured to determine that such a scenario has elapsed). By way of example only and not by way of limitation, an exemplary scenario where the recipient cannot utilize the remote device 240 could be where the recipient is in the shower, in a pool, in heavy rain, engaged in exercise playing sports, etc. It is noted that in the embodiments associated with the recipient taking a shower or swimming, etc., it is assumed that the recipient's device is a totally implanted hearing prosthesis and/or is a hearing prosthesis that has an extra component that is protected via a waterproof system (e.g., a wearable waterproof case).

It is noted that in at least some embodiments, there is utilitarian value in providing an input arrangements of the hearing prosthesis 100 that can activate a migrated functionality. In this regard, a smart phone or the like, as that term is utilized generically, has buttons or otherwise touch sensitive features that enable the recipient to activate a given functionality. While at least some embodiments include a hearing prosthesis that also includes such buttons/touchpads, alternatively and/or in addition to this, some embodiments are configured to utilize audio commands from the recipient. By way of example only and not by way of limitation, the hearing prosthesis 100 can be configured to recognize verbal commands from the recipient that indicates activation of a functionality. For example, a recipient can speak "prosthesis, create a contact." These words, or words similar thereto, would activate the functionality associated with creating a contact. The recipient would then speak the contact information, and the sound of the recipient's speech would be captured by the hearing prosthesis, and contact data will be created in the hearing prosthesis. Still further by way of example, a recipient can speak "prosthesis, provide me a reminder." These words, or words similar thereto would activate the functionality associated with providing the recipient a reminder. Other types of mechanisms can be utilized to activate a functionality.

Still further, specific commands can be utilized to initiate a hands-free and/or a remote device free mode. By way of example only and not by way of limitation, the recipient could state "free me of the smart phone." These words, or words similar thereto, would activate a hands free mode based on the hearing prosthesis 100 without the remote device.

It is further noted that in at least some exemplary embodiments, other types of commands can be utilized to initiate functionalities that are migrated to the hearing prosthesis 100. By way of example only and not by our limitation, air caps can be utilized.

Is briefly noted that there is utilitarian value with respect to a totally implantable hearing prosthesis having a subcutaneous microphone in that the system can be utilized to confirm that the recipient is speaking when verbal commands a received. In this regard, with respect to, for example, the above exemplary scenarios, the hearing prosthesis 100 may not necessarily be able to determine that the recipient has spoken the words associated with the command, or that a nonrecipient has spoken the words assisted with the command, and the hearing prosthesis 100 is simply captured those words. (That said, in at least some exemplary embodiments, the hearing prosthesis 100 is configured to identify the users voice based on frequency analysis etc., to at least decrease the likelihood that nonrecipient voice initiates one of the functionalities.) Because of features associated with a totally implantable hearing prosthesis in general, and the subcutaneous microphone in particular, features associated with own voice event determination can be utilized in conjunction with the teachings detailed herein to ensure that any verbal command is a result of the recipient speaking, and not a bystander speaking. Accordingly, in an exemplary embodiment, the system 210 is configured to identify an own voice event of the recipient and implement the functionality only upon such an identification, albeit in conjunction with another event (such as, for example, a determination that a given command has been spoken).

Figure 9:
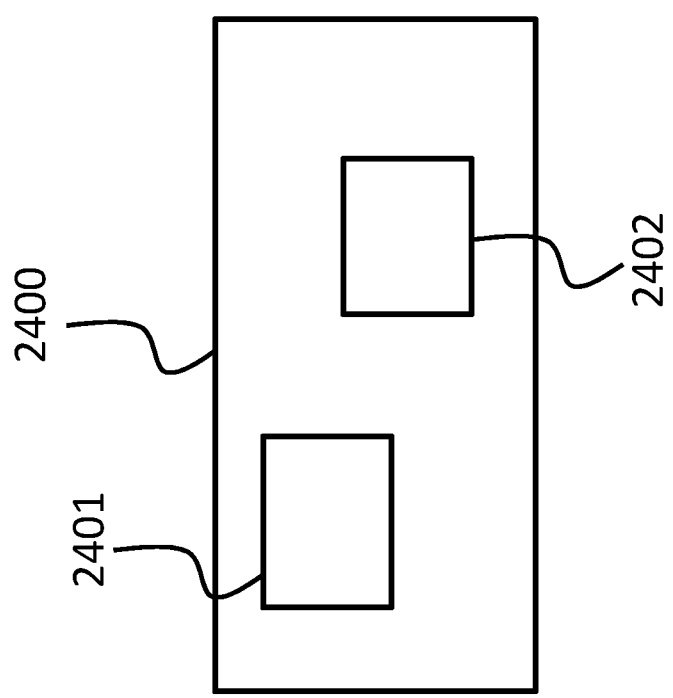
FIG. 9 an exemplary functional schematic of an exemplary hand held device according to an exemplary embodiment.

In view of the above, in an exemplary embodiment, now with reference to FIG. 9, there is a portable hand-held device 2400 (e.g., a smart phone, as that term is utilized generically), which in an exemplary embodiment, corresponds to device 240 above, having a cellular telephone communication suite 2401 and a hearing prosthesis functionality suite 2402. In an exemplary embodiment, the hearing prosthesis functionality suite 2402 is configured to at least one of perform or simulate a functionality of a hearing prosthesis, and the portable hand-held device 2400 is configured to wirelessly communicate with the hearing prosthesis. In an exemplary embodiment of this exemplary embodiment, the device 2400 is configured to receive migration input from a recipient of the hearing prosthesis and migrate a functionality of the device 2400 to the hearing prosthesis based on the migration input. By way of example only and not by way of limitation, this can be input into a user interface of the device 2400. For example, the device 2400 can include an app that the recipient of the hearing prosthesis 100 activates by touching a portion of a touchpad screen of the device 2400 displaying an icon for that app. Alternatively and/or in addition to this, the recipient can speak into the device 2400.

The migrated functionality associated with the device of FIG. 9 can be any of the applicable functionalities detailed herein and/or other functionalities, providing that technology can enable such any utilitarian manner. For example, the functionality of the hearing prosthesis is sound processing to develop data used by a stimulator of the hearing prosthesis to evoke a hearing percept. That is, by way of example only and not by way of limitation, the device 2400 could include its own sound processor that is effectively identical (including identical) to that contained in the hearing prosthesis 100.

As will be understood from the above, in an exemplary embodiment, the device 2400 is configured to automatically migrate a functionality of the device to the hearing prosthesis based on at least one of a temporal schedule or a determination of an occurrence of a predetermined event (e.g., a trigger). Some exemplary predetermined events are detailed below with respect to possible triggers that will result in automatic migration of the functionality to the hearing prosthesis.

In an exemplary embodiment, the device 2400 is configured to receive data from the hearing prosthesis 100 usable with a voice based functionality of the device (e.g., a verbal note, dictation, etc.) an execute the voiced based functionality after the data is received (e.g., prepare text based on the data and store the text as dictation, store the verbal note as an audio file, etc.).

As noted above, in an exemplary embodiment, the transfer/migration of functionality from the portable handheld device 240 can be initiated as a result of the occurrence of some predetermined triggering event. Any of the aforementioned triggering events may be applicable to the migration/transfer and thus can be utilized in at least some embodiments.

In some exemplary embodiments, some triggering events can include, for example a scenario where the portable handheld device is turned off and/or on, the portable handheld device 240 comes in and/or out of range of the hearing prosthesis 100 (i.e., the link 230 is established and/or broken), a determination is made (automatically) that the portable handheld device 240 is running low on power etc. In some exemplary embodiments, the triggering events can be periodic and/or related to an event that occurs periodically. In some exemplary embodiments, the periodic event can be based on an output of a timer (e.g., a time output of a timer, etc.).

Still further by way of example only and not by way of limitation, in an exemplary embodiment, a triggering event can correspond to the proximity of a caregiver to the hearing prosthesis 100. In an exemplary embodiment, a caregiver (e.g. parents of a small child, the latter being a recipient of the hearing prosthesis 100) of a recipient may not desire migration to take place unless he and/or she is approximate to the recipient. Such can be the case because the caregiver does not once the recipient to have to operate the remote device 240 (or even have access to the remote device 240). Accordingly, in an exemplary embodiment, the system 210 can be configured so as to automatically migrate a functionality, or at least enable the migration the functionality to the remote device 240 upon an automatic determination that a caregiver is present or otherwise proximate to the recipients of the hearing prosthesis 100. Indeed, in an exemplary embodiment, such can be a result of a caregiver with a portable handheld device, such as by way of example only and not by way of limitation, a personalized smart phone as that term is utilized in the generic sense, into proximity with the hearing prosthesis 100, which personalized smart phone What a signal to the hearing prosthesis 100 indicating that the caregiver is proximate to the recipient. (The personalized smart phone of the parent need not be the remote device 240 of the system 210—that can be a personalized smart phone, as used in the generic sense, of the recipient—the personalized smart phone of the parent is simply utilized to provide an indication of proximity of the caregiver, although in other embodiments, the personalized smart phone of the hearing prosthesis can also correspond to a remote device 240 to which functionality can be migrated. Still further, in an exemplary embodiments of a triggering event can be an environment in which the hearing prosthesis 100 is located (e.g., too noisy of an environment, to quiet in an environment, ambient light being too bright to properly evaluate LED or LCD information, etc.).

In an exemplary embodiment, an automatic triggering event can entail the remote device 240 being brought into proximity of the hearing prosthesis (e.g., as indicated by the establishment of the wireless link 230 between the two components).

In addition to trigger events associated with remote device 240 availability, other conditions can be triggering events, such as by way of example only and not by way of limitation, weather related events. For example, migration/transfer of functionality can be triggered based on a determination that it is raining, such having utilitarian value in a scenario where, for example, the recipient does not want to expose the portable handheld device 240 to the rain. Alternatively and/or in addition to this, in an exemplary embodiment, a triggering event can be associated with an activity in which a recipient is engaging. For example, a triggering event can be a determination that the recipient is jogging, driving, etc., sleeping, etc. Corollary to this is that in at least some exemplary embodiments, the system 210 is configured to automatically determine whether or not the recipient is engaging and an exemplary activity (e.g., the hearing prosthesis and/or the portable handheld device can include and accelerometer coupled with software that can extrapolate that the recipient is jogging and/or running based on the output of the accelerometer). Such capability to determine the activity in which the recipient is engaging need not necessarily be due to active sensing of such engagement. By way of example, the system 210 can deduce that a recipient is engaging in an activity based on other types of settings (e.g., the portable device 210 is being recharged from 12 V DC current, thus indicating that the recipient may be driving, the portable device 210 is located in a support device that permits hands-free use while driving, again thus indicating that the recipient may be driving, etc.).

Still further, in an exemplary embodiment, a warning of a functionality that might be migrated can entail a warning to the recipient that he or she is walking and/or driving or otherwise traveling into a certain area (a location/geographic-based warning).

Still with respect to utilizing detection of recipient activity is a trigger, in an exemplary embodiment, the hearing prosthesis 100 could detect or otherwise deduce that the recipient is underwater. In an exemplary embodiment, this can be achieved via the termination of a pressure related feature associated with the recipient. By way of example only and not by way of limitation, an exemplary embodiment implemented in a totally implantable hearing prosthesis, a variable associated with the transfer function of a membrane and/or diaphragm of a subcutaneous microphone could be analyzed. For example, an increase in pressure when the recipient skin, such as that associated with the recipient going underwater, would likely be transferred to the diaphragm/membrane of the subcutaneous microphone. That is, additional pressure would be applied to the diaphragm/membrane relative to that which would be the case if the recipient was out of the water at sea level (or higher). The hearing prosthesis can be configured to automatically determine that the transfer function has changed in a manner indicative of the recipient being exposed to pressures associated with being underwater, and thus at least deduce, if not detect that the recipient is indeed underwater. Still further by way of example only and not by way of limitation, in an exemplary embodiment, the hearing prosthesis 100 could detect water or moisture utilizing a censor thereof. Still further, in an exemplary embodiment, the hearing prosthesis could be configured to evaluate sounds and/or sound variations associated with water (e.g., based on frequencies associated with splashing of water, the sound of dripping water, the different sound of noises that travel through water relative to that which travels through air, many of which are distinct) and thus deduce that the recipient is at least swimming, if not underwater.

Still further, in an exemplary embodiment, the hearing prosthesis 100 could detect or otherwise deduce an environment and or a situation and/or a location in which the recipient is in based on environmental sounds entering the microphone. By way of example only and not by way of limitation, the sounds of birds tweeting or leaves rustling may indicate that the recipient is in a forest environment, or at least a non-urban environment. Conversely, still by way of example, the sounds of horns beeping may indicate that the recipient is in an urban environment. Still further by way of example, the sounds of water lapping against water due or fiberglass may indicate that the recipient is on a boat, and the sounds of ocean noises may indicate that the recipient is at the beach. Still further by way of example only and not by way limitation, sounds corresponding to those of the interior of a commercial jetliner can indicate that the recipient is in a commercial jetliner. Any or all of these can be a triggering event as detailed above. Is further noted that alternatively, the remote handheld device could detect or otherwise deduce the aforementioned environment and/or a situation and/or a location in which the recipient is in based on environmental sounds entering a microphone.

It is also noted that in an exemplary embodiment, some of these triggering events are age-appropriate triggering events. In this regard, an exemplary method entails executing one or all of the method actions detailed herein coupled with the method action of setting a triggering event and/or eliminating a triggering event due to the age of the recipient. Corollary to this is that in at least some exemplary embodiments, one or more or all of the method actions detailed herein are executed based on a triggering event that was set based on the age of the recipient. Another exemplary embodiment includes the non-execution of a method action because of the elimination of a triggering event that was eliminated based on the age the recipient. Accordingly, in an exemplary embodiment, there is a system 210 configured with triggers that prevents the migration/transfer of a function and/or enables the migration/transfer of a function for recipients of a certain age and not for a recipient of ages other than the certain age and/or vice versa. By way of example only and not by way of limitation, a scenario where a recipient automatically receives a hearing percept corresponding to text messages when no one is speaking to him or her might be unnerving to a small child and to a very old recipient, while such might be perfectly acceptable to a young adult.

Alternatively and/or in addition to the above, in some exemplary embodiments, the triggering events can be based on environmental conditions. By way of example, triggering events can be based on temperature (ambient and/or temperature of one or more of the components of system 210), movement, altitude (e.g. pressure altitude, altitude based on telemetric data etc.), the presence of wind (e.g., a determination that wind is present based on a wind noise detection algorithm of the system 210), etc. By way of example and not by way of limitation, a heat sensor can determine that the external component of a cochlear implant is becoming too hot (e.g., has achieved the temperature that could deleteriously affect the sound processor), and thus automatically transfer the functionality to the remote device 240.

Still further, in an exemplary embodiment, the triggering event can be based on a characteristic of a sound captured by the hearing prosthesis and/or by the remote device 240. By way of example only and not by way of limitation, if a characteristic of a sound is that of an alarm (e.g., inclement weather warning detailing three tornadoes in the vicinity of the recipient received via the remote device 240, where the remote device is a smart phone as that term is utilized generically), and such alarm would normally be presented via text message on the remote device 240, the functionality of the alarm could automatically be transferred to the hearing prosthesis 100, albeit in the form of a hearing percept. (It is further noted that in at least some instances, the transfer of the functionality will not eliminate the functionality from the transferor device. For example, in the aforementioned scenario, the remote device 240 would also present a text message announcing the impending doom.) Still further by way of example only and not by way of limitation, the characteristic can be a characteristic indicative of an own voice of the recipient. In an exemplary embodiment, there can be utilitarian value with respect to utilizing the microphone of the remote device 240 in lieu of the microphone of the hearing prosthesis 100, as the ladder microphone would be more likely to be subjected to potential deleterious effects associated with own voice scenarios.

Additional triggers can entail, by way of example, tapping the hearing prosthesis 100 and given manner (e.g. with a predetermined rhythm etc.), determination that a recipient and/or a components of the system 210 has undergone a specific type of movement (e.g. acceleration having a predetermined value or greater than a predetermined value, repeated vertical movements etc.). Still further, automatic recognition of a voice by the system 2 tend and were automatic recognition of a given sound, at least relative to other voices and/or other sounds, can be utilized as a triggering event.

Some additional triggering events that can trigger migration/transfer can include, by way of example, service of one or both components of the system 210 (planned and/or unplanned), a periodically occurring event and/or a semi-periodically occurring event (e.g. night, sleeping, waking up, eating lunch, showering, a routine travel route (bus route, scheduled flights, drive) etc.).

Still further, in an exemplary embodiment, triggering events can correspond to the elimination of the initial triggering event. For example, if the triggering event was a low battery event in one of the devices of the system 210, a subsequent triggering event to migrate the functionality back could be the determination that the battery at issue has been recharged or otherwise is being supplied with a power source that enables the battery to be recharged. Still further by way of example only and not by way of limitation, if the triggering event was a scenario in which one of the components was out of range (e.g., the wireless link 230 is broken), the subsequent triggering event that would migrate the functionality back could be the scenario where the component at issue comes back into range (e.g., the wireless link 230 is reestablished).

While the above triggering events have been detailed with respect to triggering transfer/migration of a given functionality, in at least some embodiments, the triggering events detailed herein and/or variations thereof can be further utilized as triggering events for the above noted pre-migration synchronization actions. That said, in some alternative embodiments, there are triggering events associated with pre-migration synchronization that may not necessarily be also utilize for migration/transfer. Indeed, such as come, top with the concept of "pre-migration synchronization." By way of example only and not by way of limitation, pre-migration synchronization can be triggered by the change of a setting, such as, for example, a change in alarm setting, a change in a battery reserve requirement (e.g., migration at 20% of battery charge instead of 15% or 10% of battery charge), etc.

In an exemplary embodiment, pre-migration synchronization can occur as a result of a physiological change in the recipient detected by the system 210, such as by way of example only and not by way of limitation, a heartbeat change, a body temperature change, etc.

The above automatic triggers of the pre-migration synchronization can have utilitarian value in such instances where the loss of functionality or otherwise the utilitarian value of transferring the functionality from one component of the system to tend to the other component of the system 210 may not necessarily be predictable and/or be controllable. By way of example only and not by way of limitation, a recipient can experience a scenario where he or she cannot utilize his or her smart phone, and such might be unexpected. For example, a flat battery might be unexpected. The loss of the remote device 240 and/or a scenario where the recipient leaves the remote device 240 at home while on travel could be unexpected/the inability to find the remote device 210 could be unexpected, the loss of the external component of the hearing prosthesis might be unexpected, etc.

It is noted that in at least some embodiments, any triggering event that has been described herein can be utilized for migration/transfer from the hearing prosthesis to the remote device and/or from the remote device to the hearing prosthesis if such can be enabled and is otherwise pertinent to a given migration, unless otherwise specified herein. Further, any triggering event that can enable the teachings detailed herein and/or variations thereof can be utilized in at least some embodiments.

It is further noted that any transfer and/or migration of functionality detailed herein also corresponds to a disclosure of the transfer back/the migration back of functionality to the device/component from which the migration was transferred/migrated the first instance.

Is further noted that in some exemplary embodiments, an indication can be provided to the recipient that functionality has been migrated and/or that functionality has been migrated back. By way of example only and not by way of limitation, in an exemplary embodiment, the hearing prosthesis 100 can be configured to provide a hearing percept corresponding to synthesized words indicating that functionality has been migrated from the remote device to the hearing prosthesis and/or migrated back from the remote device to the hearing prosthesis. The further by way of example only and not by way of limitation, in an exemplary embodiment, the remote device 240 can provide an indication to the recipient corresponding to a text message indicating that functionality has been migrated from the hearing prosthesis to the remote device and/or migrated back from the hearing prosthesis to the remote device.

Still further, ancillary indications can be provided as a result of migration/migration back. For example, the remote device 240 could indicate changes and/or events that have occurred since the initial migration. By way of example only and not by limitation, after migration back to the remote device, the remote device could provide a message to the recipient that 2 messages have been received since the initial migration. Still further by way of example only and not by way of limitation, one or both of the components of the system 210 can indicate how long the functionality has been migrated at the time that the functionality is migrated back and/or shortly thereafter. Corollary to this is then that an exemplary embodiment, the system 210 can periodically indicate to a recipient automatically that a functionality(s) is in a migrated status. Still further, in an exemplary embodiment, the system 210 can be configured to indicate to the recipient what functionalities are in a migrated status upon a query from the recipient. Still further, in an exemplary embodiment, data can be logged relating to the migration and migration back of the functionalities (e.g. timing of migrations, the length of time of a migration, the number of times that a migration has occurred etc.). The system 210 can be configured such that this data can be provided to the recipient and/or to another entity seeking such information.

It is noted that any feature detailed above with respect to a given component of the system 210 corresponds to a disclosure of the system 210 as a whole having that feature. Still further, it is noted that any feature detailed above with respect to the system 210 corresponds to a disclosure of one or both of the components of the system 210 having that feature. In some embodiments, any feature disclosed herein associated with the hearing prosthesis 100 can correspond to a disclosure of that feature associated with the remote device 240, and vice versa, unless otherwise specified and/or unless otherwise impractical with respect to the current state of technology. Corollary to this is that any transfer/migration detailed herein from one component of the system 210 to the other component of the system 210 corresponds to a disclosure of the transfer/migration of the functionality from the other component to the one component, as well as a disclosure of transfer/migration back from the pertinent components, unless otherwise specified herein and/or unless otherwise impractical with respect to the current state of technology. Still further, in any triggering event detailed herein relating to the transfer/migration of functionality and/or synchronization of data from one component to the other component of the system 210 corresponds to a disclosure of transfer/migration of functionality and/or synchronization of data from the other component to the one component, unless otherwise specified and/or unless otherwise impractical with respect to the current state of technology.

Moreover, it is noted that while the above concentrates on the migration of functionality between a single hearing prosthesis 100 and a single remote device 240, in an alternate embodiment, functionality can be migrated between 2 or more hearing prostheses 100 and/or 2 or more remote devices 240. By way of example only and not by way of limitation, the scenario can exist where a young child with a like utilizes a hearing prosthesis 100. The system including the hearing prosthesis 100 can also include the child's remote device along with a parents' remote device (or both parents' remote devices or even more). This concept can further be extrapolated to a scenario where an older person has the recipients, and the functionality is migrated between the hearing prosthesis and remote devices of children of the recipient. In some instances, the functionality can be migrated from the hearing prosthesis to 2 or more remote devices at the same time. In an exemplary embodiment, the resulting system can be utilized an algorithm to determine primacy between the 2 remote devices in the event of a conflict. By way of example only and not by way of limitation, primacy can be established based on which remote devices closer to the hearing prosthesis (e.g., such can be based on, for example, the strength of the resulting wireless link between the 2 devices, temporal factors associated with strands mission of signals, etc.). Any device, system, and/or method that can enable functionality migration between more than one device to another device that can enable the teachings detailed herein and/or variation thereof to be practiced can be utilized in at least some embodiments.

It is noted that any method detailed herein also corresponds to a disclosure of a device and/or system configured to execute one or more or all of the method actions associated there with detailed herein. In an exemplary embodiment, this device and/or system is configured to execute one or more or all of the method actions in an automated fashion. That said, in an alternate embodiment, the device and/or system is configured to execute one or more or all of the method actions after being prompted by a human being. It is further noted that any disclosure of a device and/or system detailed herein corresponds to a method of making and/or using that the device and/or system, including a method of using that device according to the functionality detailed herein.

It is noted that embodiments include non-transitory computer-readable media having recorded thereon, a computer program for executing one or more or any of the method actions detailed herein. Indeed, in an exemplary embodiment, there is a non-transitory computer-readable media having recorded thereon, a computer program for executing at least a portion of any method action detailed herein.

It is further noted that any disclosure of a device and/or system detailed herein also corresponds to a disclosure of otherwise providing that device and/or system.

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. An apparatus, comprising:
a sensory supplement medical device configured to implement a first functionality and second functionality, wherein the second functionality is different from the first functionality, wherein
the sensory supplement medical device includes a stimulation device, wherein the stimulation device is configured to implement the first functionality of the sensory supplement medical device, wherein the first functionality is a functionality corresponding to the providing of sensory supplement to a recipient of the sensory supplement medical device to evoke a sensory percept, wherein
the second functionality is sound capture functionality,
the sensory supplement medical device is a hearing prosthesis,
the hearing prosthesis is configured to automatically migrate the second functionality to a device remote from the hearing prosthesis, and
the hearing prosthesis is configured to automatically perform an assessment of a status of at least one of the hearing prosthesis or the device remote from the hearing prosthesis and prevent the automatic migration of the second functionality based on the assessment.

2. The apparatus of claim 1, wherein:
the sensory supplement medical device is configured to implement a third functionality, the third functionality being an alert to the recipient of the sensory supplement medical device; and
the sensory supplement medical device is configured to migrate the third functionality to the device remote from the sensory supplement medical device.

3. The apparatus of claim 1, wherein:
the sensory supplement medical device is configured such that all control inputs of the sensory supplement medical device based on manual input into the sensory supplement medical device by the recipient can be controlled by the remote device upon migration of the second functionality to the remote device.

4. A system, comprising:
the apparatus of claim 1; and
the device remote from the sensory supplement medical device.

5. The apparatus of claim 1, wherein:
the device remote from the sensory supplement medical device is a smart phone.

6. The apparatus of claim 1, wherein the sensory supplement medical device is configured such that:
the sensory supplement medical device automatically suspends execution of the second functionality by the sensory supplement medical device upon a determination that a power level of a power storage device thereof meets a given criteria and automatically migrates the second functionality to the device remote from the sensor supplement medical device upon the determination.

7. The apparatus of claim 1, wherein:
the remote device is configured to execute the second functionality and communicate the results to the sensory supplement medical device; and
the sensory supplement medical device is configured to evoke a sensory percept based on the communicated results.

8. The apparatus of claim 1, wherein:
the sensory supplement medical device is configured to automatically wirelessly communicate data based on captured speech to the remote device upon an automatic determination by the sensory supplement medical device that the sensory supplement medical device cannot evoke a sensory percept based on the captured speech so that the remote device is enabled to automatically display text corresponding to a speech content of the captured speech wirelessly communicated.

9. The apparatus of claim 1, wherein:
the sensory supplement medical device is configured to implement a third functionality, the third functionality being an alert to the recipient;
the sensory supplement medical device is configured to migrate the third functionality to the device remote from the sensory supplement medical device; and
the alert to the recipient is an alert indicative of at least one of:
 a transcutaneous communication link of the hearing prosthesis between an implantable component thereof and an external component thereof is at least partially disrupted;
 a signal from an acoustic component of the hearing prosthesis is not being received in a sufficient manner such that the first functionality can be enabled;
 a power storage device of the hearing prosthesis has achieved a predetermined status; or
 the hearing prosthesis has experienced an internal software fault.

10. The apparatus of claim 1, wherein:
the sensory supplement medical device is configured to implement a third functionality, the third functionality being conveyance of a status to the recipient;
the sensory supplement medical device is configured to migrate the third functionality to the device remote from the sensory supplement medical device; and
the status to the recipient is a status indicative of at least one of:
 the hearing prosthesis is evoking a hearing percept based on audio streaming thereto; or
 the hearing prosthesis is in a sound management mode corresponding to at least one of scene classification or noise reduction.

11. The apparatus of claim 1, wherein:
the sensory supplement medical device is configured to implement a third functionality, the third functionality being the processing of ambient sound;
the sensory supplement medical device is configured to migrate the third functionality to the device remote from the sensory supplement medical device;
the hearing prosthesis is configured to evoke a hearing percept based on communicated results of the processing of ambient sound to the hearing prosthesis from the device remote from the sensory supplement medical device after the migration;
the hearing prosthesis is at least partially implanted in the recipient; and
the recipient has a hearing disability and the hearing prosthesis helps the recipient to hear.

12. The apparatus of claim 1, wherein:
the sensory supplement medical device is configured to implement a third, a fourth and a fifth functionality all different from each other and all different from the first functionality; and
the sensory supplement medical device is configured to migrate the third, fourth and fifth functionality to the device remote from the sensory supplement medical device.

13. The apparatus of claim 1, wherein:
the sensory supplement medical device is configured to operate based on data from the device remote from the sensory supplement medical device, wherein the data is based on the migrated second functionality executed by the device remote from the sensory supplement medical device.

14. The apparatus of claim 1, wherein:
the hearing prosthesis is a hybrid hearing prosthesis.

15. The apparatus of claim 1, wherein:
the hearing prosthesis is one of solely a cochlear implant, solely a bone conduction device or solely a middle ear implant.

16. The apparatus of claim 1, wherein:
the hearing prosthesis is configured to stimulate a recipient to evoke a hearing percept based on ambient sound only by electrical stimulation.

17. An apparatus, comprising:
a sensory supplement medical device configured to implement a first functionality and second functionality, wherein the second functionality is different from the first functionality, wherein
the sensory supplement medical device includes a stimulation device, wherein the stimulation device is configured to implement the first functionality of the sensory supplement medical device,
the first functionality is a functionality corresponding to the providing of sensory supplement to a recipient of the sensory supplement medical device to evoke a sensory percept,
the second functionality is sound capture functionality,
the sensory supplement medical device is a hearing prosthesis,
the hearing prosthesis is configured to automatically migrate the second functionality to the device remote from the hearing prosthesis upon both of:
 a determination that a power storage device of the hearing prosthesis has achieved a predetermined status; and
 the migration of the second functionality will prolong the first functionality relative to that which would be the case in the absence of the migration of the second functionality.

18. The apparatus of claim 17, wherein:
the sensory supplement medical device is configured to implement a third functionality, the third functionality being conveyance of a status to the recipient;
the sensory supplement medical device is configured to migrate the third functionality to the device remote from the sensory supplement medical device; and
the status to the recipient is a status indicative of at least one of:
 the hearing prosthesis is evoking a hearing percept based on audio streaming thereto; or the hearing prosthesis is in a sound management mode corresponding to at least one of scene classification or noise reduction.

19. The apparatus of claim 17, wherein:

the device remote from the hearing prosthesis is a non-hearing prosthesis device.

20. The apparatus of claim 17, wherein:

the sensory supplement medical device is configured such that all control inputs of the sensory supplement medical device based on manual input into the sensory supplement medical device by the recipient can be controlled by the remote device upon migration of the second functionality to the remote device.

21. A system, comprising:

the apparatus of claim 17; and the device remote from the sensory supplement medical device.

22. The apparatus claim 21, wherein:

the device remote from the sensory supplement medical device is a smart phone.

23. The apparatus of claim 17, wherein the sensory supplement medical device is configured such that:

the sensory supplement medical device automatically suspends execution of the second functionality by the sensory supplement medical device upon a determination that a power level of a power storage device thereof meets a given criteria and automatically migrates the second functionality to the device remote from the sensor supplement medical device upon the determination.

24. The apparatus of claim 17, wherein:

the remote device is configured to execute the second functionality and communicate the results to the sensory supplement medical device; and the sensory supplement medical device is configured to evoke a sensory percept based on the communicated results.

* * * * *